United States Patent
Iwata et al.

(10) Patent No.: US 7,196,080 B2
(45) Date of Patent: Mar. 27, 2007

(54) PHENYLPYRIDINECARBONYLPIPERAZINE DERIVATIVE

(75) Inventors: Masahiro Iwata, Tsukuba (JP); Noriyuki Kawano, Tsukuba (JP); Hiroyuki Kaizawa, Tsukuba (JP); Tomofumi Takuwa, Tsukuba (JP); Issei Tsukamoto, Tsukuba (JP); Ryushi Seo, Tsukuba (JP); Kiyoshi Yahiro, Itabashi-ku (JP); Miki Kobayashi, Tsukuba (JP); Makoto Takeuchi, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 221 days.

(21) Appl. No.: 10/480,543

(22) PCT Filed: Jun. 13, 2002

(86) PCT No.: PCT/JP02/05926

§ 371 (c)(1),
(2), (4) Date: Dec. 12, 2003

(87) PCT Pub. No.: WO02/102778

PCT Pub. Date: Dec. 27, 2002

(65) Prior Publication Data

US 2004/0192701 A1 Sep. 30, 2004

(30) Foreign Application Priority Data

Jun. 15, 2001 (JP) .............................. 2001-182296

(51) Int. Cl.
*A61K 31/496* (2006.01)
*C07D 401/06* (2006.01)
*C07D 401/14* (2006.01)
*C07D 413/14* (2006.01)
*C07D 213/79* (2006.01)

(52) U.S. Cl. .............................. 514/227.5; 514/235.8; 514/252.02; 514/252.11; 514/252.18; 514/253.06; 514/253.09; 514/253.11; 514/253.13; 544/58.2; 544/58.6; 544/121; 544/238; 544/295; 544/357; 544/363; 544/364; 544/365

(58) Field of Classification Search ................. 546/326; 544/364, 365
See application file for complete search history.

(56) References Cited

U.S. PATENT DOCUMENTS 6,849,660 B1 * 2/2005 Jefferson et al. ............ 514/471

FOREIGN PATENT DOCUMENTS

| EP | 0 034 349 A2 | 8/1981 |
| WO | WO 94/12461 A1 | 6/1994 |
| WO | WO 96-40636 A1 | 12/1996 |

OTHER PUBLICATIONS

Dyke et al. Expert Opin.Invest. Drugs, vol. 11, p. 1-13 (2002).*
Ahmad, D., et al., Bioconversion of 2-hydroxy-6-oxo-6-(4'-chlorophenyl) hexa-2, 4-dienoic acid, the meta-cleavage product of 4-chlorobiphenyl., J. Gen. Microbiol., 1991, vol. 137, No. 6, p. 1375-1385.
Honma, Y., et al., Antiallergic agents. 2. N-(1HTetrazol-5-yl)-6-phenyl-2-pyridinecarbo-xamides., J. Med, Chem., 1983, vol. 26, No. 10, p. 1499-1504.

* cited by examiner

*Primary Examiner*—Emily Bernhardt
(74) *Attorney, Agent, or Firm*—Sughrue Mion, PLLC

(57) ABSTRACT

The present invention relates to a compound which is represented by the following general formula and has type 4 phosphodiesterase inhibitory action, and uses and an intermediate compound thereof.

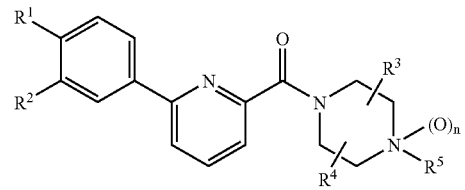

(wherein
R1, R2: hydrogen, a halogen, a lower alkyl, a lower alkoxy, or the like,
R3, R4: hydrogen, a (substituted) lower alkyl, a halogen, or the like,
R5: hydrogen, a lower alkyl, a lower alkoxycarbonyl, or the like, and
n: 0 or 1).

7 Claims, No Drawings

PHENYLPYRIDINECARBONYLPIPERAZINE DERIVATIVE

TECHNICAL FIELD

The present invention relates to a phenylpyridinecarbonylpiperazine derivative useful as a medicament, particularly as a type 4 phosphodiesterase (PDE4) inhibitor.

BACKGROUND ART

Asthma which has been hitherto considered as a reversible obstruction of airway is currently understood as a disease characterized by airway hypersensitivity and airway obstruction derived from chronic airway inflammation involving a number of inflammatory cells. The number of the patients has been increasing steadily and is predicted to further increase hereafter.

For the treatment of asthma, inhale steroid drugs as antiinflammatory agents, and β-stimulants such as procaterol and xanthine derivatives such as aminophylline and theophylline as bronchodilators are now mainly used.

The inhale steroid drugs have a wide antiinflammatory action and are highly useful as asthma-treating drugs, but the necessity of instructing an appropriate inhalation method and the existence of steroid-resistant asthma patients have been pointed out (ASTHMA 13-1, 69–73 (2000), Internal Medicine, 81, 485–490 (1998)).

The bronchodilators alleviate contraction of airway smooth muscle by increasing intracellular cyclic adenosine 3',5'-monophosphate (cAMP) concentration through the activation of an intracellular CAMP producing enzyme, adenylate cyclase, or the inhibition of a CAMP hydrolyzing enzyme, phosphodiesterase (PDE) in airway smooth muscle (Internal Medicine, 69, 207–214 (1992)). It is known that increased intracellular CAMP concentration induces inhibition of the contraction of airway smooth muscle (Clin. Exp. Allergy, 22, 337–344 (1992), Drugs of the Future, 17, 799–807 (1992)), which is effective in improving conditions of asthma.

However, it is known that the xanthine derivatives express systemic side effects such as hypotension and cardiotonic action (J. Cyclic Nucleotide and Protein Phosphorylation Res., 10, 551–564 (1985), J. Pharmacol. Exp. Ther., 257, 741–747 (1991)), and the β-stimulants are apt to cause desensitization and, when the dosage is increased, generate side effects such as finger tremor and palpitation.

On the other hand, chronic obstructive pulmonary disease (COPD) is a respiratory disease which relates to an abnormal inflammatory reaction and is characterized by irreversible limitation of airflow, and is the fourth cause of death in the world at present (Executive summary. Global Initiative for Chronic Obstructive Lung Disease (GOLD), (2000)). Currently, as in the case of asthma, β-stimulators, anticholinergic drugs, and xanthine derivatives such as aminophylline and theophylline as bronchodilators are now generally used as drug therapy for COPD. In addition, inhale steroid drugs are also used since attention has been attracted to the fact that the presence of chronic inflammation in airway participates in the obstructive disorder also in COPD, but it has been reported that continuous treatment with inhale steroid does not improve the long-term decrease of FEV1 in COPD patients (N. Engl. J. Med. 340, 1948–53 (1999), Lancet 353, 1819–23 (1999), BMJ 320, 1297–303 (2000), N. Engl. J. Med. 343, 1902–9 (2000)). Thus, an antiinflammatory drug capable of improving conditions of COPD is highly desired.

It has been revealed that PDE is divided into at least seven families of from PDE1 to PDE7, and each of them has different distribution or function (Prog. Nucleic Acid Res. Mol. Biol. 63, 1–38 (1999)). Particularly, PDE4 does not act upon cyclic guanosine 3',5'-monophosphate (cGMP) but specifically hydrolyze cAMP among nucleotides, and its presence is recognized in both of airway smooth muscle and infiltrating cells.

Also, it has been reported that PDE4 inhibitors show inhibitory action upon eosinophiles infiltration by antigens and platelet-activating factors in guinea pig (Eur. J. Pharmacol., 255, 253–256 (1994)) and inhibit liberation of detrimental proteins (MBP, ECP) from eosinophiles (Br. J. Pharmacol., 115, 39–47 (1995)). It has been also reported that they show inhibitory action upon the contraction of airway smooth muscle by contractile substances (histamine, methacholine, LTD$_4$) (Br. J. Pharmacol., 113, 1423–1431 (1994)), inhibit production of IL-4, a cytokine which is said to deeply participate in asthma (J. Invest. Dermatol., 100, 681–684 (1993)), express inhibitory action upon the acceleration of vascular permeability in the airway (Fundam. Clin. Pharmacol., 6, 247–249 (1992)) and show inhibitory action upon airway hypersensitivity (Eur. J. Pharmacol., 275, 75–82 (1995)). Thus, a PDE4 inhibitor is expected to be an asthma-treating agent.

Moreover, it has been reported that PDE4 inhibitors have infiltration inhibitory action upon neutrophiles which are considered to be involved in airway inflammation in COPD (Pulm. Pharmacol. Ther. 2001 March; 14(2): 157–164). Furthermore, PDE4 inhibitors are capable of improving respiratory function of COPD patients (Clin. Exp. Allergy. 1999 June; 29 Suppl 2: 99–109). Thus the inhibitor is also expected to be a COPD-treating drug.

As a compound having PDE4 inhibitory activity, the following compound:

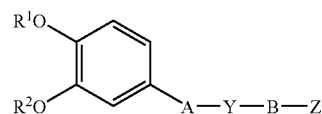

(wherein A, Y and B mean each a bond or the like, Z means a pyridine ring or the like which may be substituted with $R^3$, $R^3$ means $CONR^4R^5$ or the like, and $R^4$ and $R^5$ represent each (1) a saturated or unsaturated five- or six-membered heterocycle which may be substituted with one or two groups selected from $C_{1-4}$ alkyl, $CO_2R^7$, $CONH_2$, $CON(CH_3)_2$, oxo, OH, $NH_2$ and $N(CH_3)_2$, (2) a saturated or unsaturated six-membered heterocycle having one hetero atom as an additional ring atom selected from O, S, NH, $NCH_3$, $NCOCH_3$ or $NCH_2Ph$, or (3) a quinoline ring which may be substituted by fluorine, or the like) is disclosed in WO 94/12461. However, a part of phenylpyridinecarbonylpiperazine derivatives are included in the wide claims of the publication but no specific compound thereof is described therein. Even as phenylpyridinecarboxamide derivatives, the publication only describes the following 5-phenylpyridine-3-carboxamide.

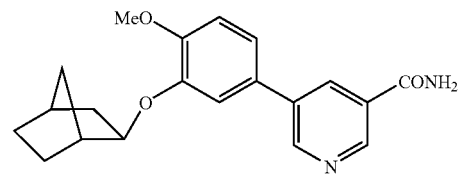

DISCLOSURE OF THE INVENTION

The inventors have conducted extensive studies on compounds having an orally available satisfactory inhibitory activity upon PDE4. As a result, they have found that a novel pyridine-2-carbonylpiperazine derivative having a phenyl group at the 6-position has a potent PDE4 inhibitory activity, and thus they have accomplished the invention.

Namely, the invention relates to a novel phenylpyridinecarbonylpiperazine derivative represented by the following general formula (I) or a pharmaceutically acceptable salt thereof and a medicament containing the same as the active ingredient.

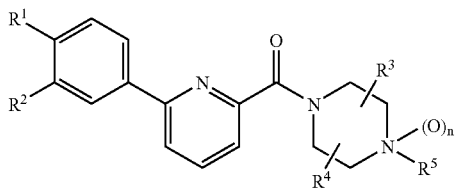

(wherein each symbol has the following meaning:

$R^1$ and $R^2$: the same or different from each other, H, a halogen, a lower alkyl, O-a lower alkyl, O-(a lower alkyl substituted with halogen(s)), $NH_2$, NH-a lower alkyl, N(a lower alkyl)$_2$, NHCO-a lower alkyl, O-a lower alkylene-NH-a lower alkyl, O-a lower alkylene-N(a lower alkyl)$_2$, O-a lower alkylene-$CO_2R^0$, O-a lower alkylene-a hydrocarbon ring or O-a lower alkylene-a heterocycle, or $R^1$ and $R^2$ are combined to form —O-a lower alkylene-O—, $R^0$: H, a lower alkyl or CH$_2$— (an optionally substituted phenyl), $R^3$ and $R^4$: the same or different from each other, H, an optionally substituted lower alkyl, a halogen, $CO_2R^0$, $CONH_2$, CON($R^0$)-(an optionally substituted lower alkyl), an optionally substituted hydrocarbon ring, an optionally substituted heterocycle, CO-(an optionally substituted lower alkyl), CO-(an optionally substituted hydrocarbon ring), CO-(an optionally substituted heterocycle) or CN, or $R^3$ and $R^4$ are combined to form a lower alkylene or oxo, $R^5$: H, a lower alkyl, $CO_2R^0$, $CONH_2$, CON($R^0$)-a lower alkyl, an optionally substituted hydrocarbon ring, an optionally substituted heterocycle, a lower alkylene-an optionally substituted hydrocarbon ring, a lower alkylene-an optionally substituted heterocycle, a lower alkenylene-an optionally substituted hydrocarbon ring, a lower alkenylene-an optionally substituted heterocycle, an lower alkylene-$R^{51}$, a lower alkylene-$CO_2R^0$, CO-a lower alkyl, CO-(an optionally substituted hydrocarbon ring), CO-(an optionally substituted heterocycle), CO-a lower alkylene-(an optionally substituted hydrocarbon ring), CO-a lower alkylene-(an optionally substituted heterocycle), CO—O-a lower alkylene-(an optionally substituted hydrocarbon ring), CO—O-a lower alkylene-(an optionally substituted heterocycle), CON($R^0$)($R^{56}$), C($R^{53}$)($R^{54}$)—$R^{55}$ or a lower alkylene-C($R^{53}$)($R^{54}$)—$R^{55}$, $R^{51}$: CO-a lower alkyl, CO-(an optionally substituted hydrocarbon ring), CO-(an optionally substituted heterocycle), CO-a lower alkylene-(an optionally substituted hydrocarbon ring), CO-a lower alkylene-(an optionally substituted heterocycle), CN, OH, O-a lower alkyl, O— (an optionally substituted hydrocarbon ring), O— (an optionally substituted heterocycle), O-a lower alkylene-(an optionally substituted hydrocarbon ring), O-a lower alkylene-(an optionally substituted heterocycle), S-a lower alkyl, S— (an optionally substituted hydrocarbon ring), S— (an optionally substituted heterocycle), S-a lower alkylene-(an optionally substituted hydrocarbon ring), S-a lower alkylene-(an optionally substituted heterocycle), NH($R^0$), N($R^0$)$_2$, N($R^0$)-(an optionally substituted hydrocarbon ring), N($R^0$)-(an optionally substituted heterocycle), N($R^0$)-a lower alkylene-(an optionally substituted hydrocarbon ring), N($R^0$)-a lower alkylene-(an optionally substituted heterocycle), N($R^0$)CO-a lower alkyl, N($R^0$)CO-(an optionally substituted hydrocarbon ring), N($R^0$)CO-(an optionally substituted heterocycle), N($R^0$)CO-a lower alkylene-(an optionally substituted hydrocarbon ring), N($R^0$)CO-a lower alkylene-(an optionally substituted heterocycle), N($R^0$)CO—O-a lower alkyl, N($R^0$)CO—O-a lower alkylene-(an optionally substituted hydrocarbon ring) or N($R^0$)CO—O-a lower alkylene-(an optionally substituted-heterocycle)

$R^{53}$, $R^{54}$ and $R^{55}$: the same or different from one another, H, a lower alkyl, $CO_2R^0$, CON($R^0$)($R^{56}$), $R^{51}$, or $R^{56}$, $R^{56}$: an optionally substituted hydrocarbon ring, an optionally substituted heterocycle, a lower alkylene-an optionally substituted hydrocarbon ring, a lower alkylene-an optionally substituted heterocycle, a lower alkylene-$R^{51}$ or a lower alkylene-$CO_2R^0$, n: 0 or 1, provided that (1) when $R^5$ is a group bonded with CO, or H, n represents 0, and (2) when both of $R^3$ and $R^4$ are each H, $R^5$ represents a group other than methyl, acetyl or benzyl; the same shall apply hereinafter).

Also, according to the invention, there is provided a medicament, particularly a PDE4 inhibitor, which comprises the phenylpyridinecarbonylpiperazine derivative or a salt thereof.

The following describes the invention in detail.

The term "alkyl", "alkylene" and "alkenylene" as used herein each means a straight or branched hydrocarbon chain. The "lower alkyl" is an alkyl group having from 1 to 6 carbon atoms, preferably an alkyl group having from 1 to 4 carbon atoms, more preferably methyl or ethyl. The "lower alkylene" means a divalent group formed by removing any one hydrogen atom from the above "lower alkyl" and is preferably an alkylene having from 1 to 4 carbon atoms, more preferably methylene, ethylene or propylene. The "lower alkenylene" means a group having one or more double bonds at any position in the "lower alkylene" having two or more carbon atoms, and is preferably an alkenylene having from 2 to 4 carbon atoms.

The "halogen" represents F, Cl, Br or I. The "lower alkyl substituted with halogen(s)" means, for example, a lower alkyl substituted with one or more halogens, and is preferably a $C_{1-6}$ alkyl substituted with one or more fluorines, more preferably fluoromethyl, difluoromethyl, trifluoromethyl or trifluoroethyl.

The "hydrocarbon ring" means a monocyclic to tricyclic hydrocarbon ring having from 3 to 14 carbon atoms, and includes a cycloalkyl, a cycloalkenyl and an aromatic hydrocarbon, and a bridged cycloalkyl and a spiro ring. Also, they may be condensed each other to form indanyl, tetrahydronaphthyl or the like.

The "cycloalkyl" is preferably a cycloalkyl having from 3 to 8 carbon atoms, more preferably cyclopropyl, cyclopentyl or cyclohexyl. The "cycloalkenyl" is preferably a cycloalkenyl having from 5 to 8 carbon atoms, more preferably cyclohexenyl. The "aromatic hydrocarbon" means an aromatic hydrocarbon group having from 6 to 14 carbon atoms, and is preferably phenyl or naphthyl, more preferably phenyl. The "bridged cycloalkyl" is preferably norbornyl or adamantyl.

The "heterocycle" is a saturated or unsaturated monocyclic to tricyclic three- to eight-membered, preferably five- to seven-membered heterocycle having, as ring atom(s), from 1 to 4 hetero atoms selected from O, S and N, which may be condensed with each other or with a cycloalkyl ring or benzene ring to form a bicyclic or tricyclic heterocycle. The ring atom, S or N may be oxidized to form an oxide or dioxide. The heterocycle includes a saturated heterocycle, an aromatic heterocycle, and a partially saturated heterocycle thereof, and in the saturated heterocycle and partially saturated heterocycle, any carbon atom(s) may be substituted with an oxo group. Moreover, the heterocycle may be bridged or may form a spiro ring, which includes an acetal ring derived from an oxo group, such as 1,3-dioxolan. The heterocycle is preferably a five- to seven-membered saturated or unsaturated monocyclic heterocycle, and is more preferably pyrrolidine, pyridine, piperidine, morpholine, thiophene, thiazole, imidazole, tetrazole, pyrazine or piperazine.

The term "optionally substituted" means "unsubstituted" or "having from 1 to 5 substituents which may be the same or different from one another".

The substituent in the "optionally substituted lower alkyl" is a hydrocarbon ring, a heterocycle, $CO_2R^0$ or a group described in $R^{51}$.

The substituent in the "optionally substituted hydrocarbon ring" or the "optionally substituted heterocycle" is preferably a group selected from the following G group.

G group: groups represented by (i) —X-a $C_{1-6}$ alkylene-A, (ii) -a $C_{1-6}$ alkylene-A, or (iii) —B.

X is O, S, SO, $SO_2$, NH, N(a $C_{1-6}$ alkyl), $SO_2NH$, $SO_2N$(a $C_{1-6}$ alkyl), $NHSO_2$, N(a $C_{1-6}$ alkyl)$SO_2$, CO, $CO_2$, O—CO, CONH, CON(a $C_{1-6}$ alkyl), NHCO, N(a $C_{1-6}$ alkyl)CO or NHCONH, A is —CN, —OH, —$CO_2H$, —$CO_2$-a $C_{1-6}$ alkyl, —$NO_2$, —$SO_3H$, —$NH_2$, —$CONH_2$, —$SO_2NH_2$, a $C_{1-6}$ alkyl substituted with halogen(s), —NH-a $C_{1-6}$ alkylene-O-a $C_{1-6}$ alkyl, —N(a $C_{1-6}$ alkyl)-a $C_{1-6}$ alkylene-O-a $C_{1-6}$ alkyl, —N(—$C_{1-6}$ alkylene-O-a $C_{1-6}$ alkyl)$_2$, -a hydrocarbon ring, -a heterocycle, —X-a $C_{1-6}$ alkyl, —X-a $C_{1-6}$ alkyl substituted with halogen(s), —X-a hydrocarbon ring, —X-a heterocycle, —X-a $C_{1-6}$ alkylene-CN, —X-a $C_{1-6}$ alkylene-OH, —X-a $C_{1-6}$ alkylene-$CO_2H$, —X-a $C_{1-6}$ alkylene-$CO_2$-a $C_{1-6}$ alkyl, —X-a $C_{1-6}$ alkylene-$NO_2$, —X-a $C_{1-6}$ alkylene-$SO_3H$, —X-a $C_{1-6}$ alkylene-$NH_2$, —X-a $C_{1-6}$ alkylene-$CONH_2$, —X-a $C_{1-6}$ alkylene-$SO_2NH_2$, —X-a $C_{1-6}$ alkylene-a hydrocarbon ring or —X-a $C_{1-6}$ alkylene-a heterocycle, B is -a $C_{1-6}$ alkyl, -a halogen, a $C_{1-6}$ alkyl substituted with halogen(s), or a group described in A.

The hydrocarbon ring and heterocycle in the above A and B herein may have from 1 to 5 substituents selected from a $C_{1-6}$ alkyl, a halogen, a $C_{1-6}$ alkyl substituted with halogen(s), CN, OH, O-a $C_{1-6}$ alkyl, $NH_2$, —NH-a $C_{1-6}$ alkyl, —N(a $C_{1-6}$ alkyl)$_2$, S-a $C_{1-6}$ alkyl, SO-a $C_{1-6}$ alkyl, $SO_2$-a $C_{1-6}$ alkyl, $SO_2NH_2$, $SO_2NH$-a $C_{1-6}$ alkyl, $SO_2N$(a $C_{1-6}$ alkyl)$_2$, $NHSO_2$-a $C_{1-6}$ alkyl, $CO_2H$, $CO_2$-a $C_{1-6}$ alkyl, $CONH_2$, CONH-a $C_{1-6}$ alkyl, CON(a $C_{1-6}$ alkyl)$_2$ and NHCO-a $C_{1-6}$ alkyl.

The substituent in the "optionally substituted phenyl" is a group shown in the above G group, preferably a $C_{1-6}$ alkyl, O-a $C_{1-6}$ alkyl or a halogen.

Preferable compounds in the invention are the following compounds:

The compounds wherein $R^1$ is O-a $C_{1-6}$ alkyl, more preferably O-a $C_{1-4}$ alkyl, particularly preferably O-methyl. The compounds wherein $R^2$ is a halogen, O-a $C_{1-6}$ alkyl or O-a $C_{1-6}$ alkylene-a hydrocarbon ring, more preferably a halogen, O-a $C_{1-4}$ alkyl or O—$CH_2$-a $C_{3-8}$ cycloalkyl, particularly preferably O-methyl. The compounds wherein $R^3$ and $R^4$ are each H, a $C_{1-6}$ alkyl, or oxo, more preferably H or methyl, particularly preferably H. Particularly preferably, the compounds wherein both of $R^1$ and $R^2$ are each O-methyl, both of $R^3$ and $R^4$ are each H, and n is 0. Moreover, the compounds wherein $R^5$ is an optionally substituted hydrocarbon ring or an optionally substituted heterocycle, more preferably an optionally substituted phenyl or an optionally substituted pyridyl, the phenyl or pyridyl having one or two groups, preferably one group selected from the above G group.

Particularly preferable compounds in the invention are the following compounds: 1-[6-(3,4-dimethoxyphenyl)pyridine-2-carbonyl]-4-(4-methoxyphenyl)piperazine, 1-(4-{4-[6-(3-cyclopropylmethoxy-4-methoxyphenyl)pyridine-2-carbonyl]piperazin-1-yl}phenyl)ethanone, 1-(6-bromo-2-pyridyl)-4-[6-(3,4-dimethoxyphenyl)pyridine-2-carbonyl] piperazine, 4'-{4-[6-(3,4-dimethoxyphenyl)pyridine-2-carbonyl]piperazin-1-yl}acetanilide, 3-diethylamino-4'-{4-[6-(3,4-dimethoxyphenyl)pyridine-2-carbonyl]piperazin-1-yl}propananilide, 4-(4-{4-[6-(3,4-dimethoxyphenyl)pyridine-2-carbonyl]piperazin-1-yl}phenyl)morpholine, 1-[2-(4-{4-[6-(3,4-dimethoxyphenyl)pyridine-2-carbonyl]piperazin-1-yl}phenoxy)ethyl]piperidin-4-ol, 4-{2-[(6-{4-]6-(3,4-dimethoxyphenyl)pyridine-2-carbonyl)piperazin-1-yl}-3-pyridyl}oxylethyl)morpholine, trans-5-(4-{4-[6-(3,4-dimethoxyphenyl)pyridine-2-carbonyl]-2,5-dimethylpiperazin-1-yl}phenyl)pentanoic acid and 1-[6-(3,4-dimethoxyphenyl)pyridine-2-carbonyl]-4-{4-[(1-oxido-4-pyridyl)methoxy]phenyl}piperadine.

Depending on the kinds of substituents, the compounds of the invention may exist in the form of geometrical isomers and tautomers, and isolated forms or mixtures of these isomers are included in the invention.

Also, the compounds of the invention may have asymmetric carbon atoms in some cases, and (R) and (S) forms of optical isomers can exist based on these atoms. The invention includes all the mixtures and isolated ones of these optical isomers.

Furthermore, pharmacologically acceptable prodrugs are also included in the compounds of the invention. The pharmacologically acceptable prodrugs are compounds having groups which can be converted into certain groups of the invention such as $NH_2$, OH and $CO_2H$ by solvolysis or under a physiological condition. Examples of the groups which form prodrugs include those which are described in Prog. Med., 5, 2157–2161 (1985) and "Iyakuhin no Kaihatsu (Pharmaceutical Research and Development)" (Hirokawa Publishing Co., 1990) Vol. 7 Drug Design 163–198.

The compounds of the invention may form acid addition salts or, depending on the kinds of the substituents, salts with bases. Such salts are pharmaceutically acceptable salts, and their illustrative examples include acid addition salts with inorganic acids such as hydrochloric acid, hydrobromic acid, hydroiodic acid, sulfuric acid, nitric acid and phosphoric acid and organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid and glutamic acid, salts with inorganic bases such as sodium, potassium, magnesium, calcium and aluminum and organic bases such as methylamine, ethylamine, ethanolamine, lysine and ornithine, and ammonium salts.

In addition, the invention also includes various hydrates, solvates and polymorphic substances of the compound (I) of the invention and salts thereof.

(Production Method)

The compound of the invention and pharmaceutically acceptable salts thereof can be produced by applying various known synthetic methods making use of the characteristics based on its fundamental skeleton or the kind of substituent. In that case, depending on the kind of functional group, it is sometimes effective from the production technical point of view to protect the functional group with an appropriate protective group or replace the group by a group, which can be easily converted into the functional group, at the starting material or intermediate stage. As such functional groups, there may be mentioned, for example, the groups described in "Protective Groups in Organic Synthesis (3rd Ed.)" edited by T. W. Greene and P. G. M. Wuts, which may be optionally used in response to the reaction conditions. In such a method, after the protective group is introduced and then a reaction is carried out, the desired compound can be obtained by removing the protecting group or converting the group into the desired group as occasion demands. Moreover, as in the above protective group, the prodrug of the compounds of the invention can be produced by introducing a specific group or carrying out a reaction using the obtained compound of the invention at the starting material or intermediate stage. The reaction can be carried out by applying a known method such as usual esterification, amidation, or dehydration by those skilled in the art.

First Production Method

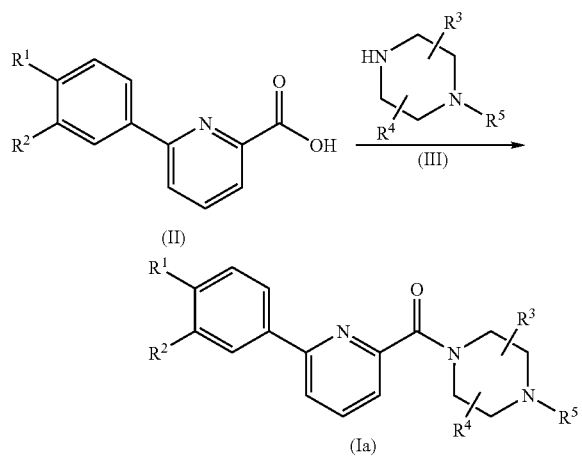

This production method is a method for producing the compound (Ia) of the invention from a carboxylic acid compound (II) by amidation.

The reaction can be carried out by condensing the compound (II) with a piperazine compound (III) in the presence of a condensing agent such as dicyclohexylcarbodiimide (DCC), diisopropylcarbodiimide (DIPC), 1-ethyl-3-(3-dimethylaminopropyl)carbodiimide (WSC) or 1,1'-carbonylbis-1H-imidazole (CDI) and optionally a further additive such as N-hydroxysuccinimide (HONSu) or 1-hydroxybenzotriazole (HOBt). Alternatively, an active-ester compound of the compound (II) with the above additive may be once isolated and then condensed with the piperazine compound (III). Examples of the solvent include aromatic hydrocarbons such as benzene, toluene and xylene; ethers such as diethyl ether, tetrahydrofuran (THF), 1,4-dioxane and dimethoxyethane; halogenated hydrocarbons such as dichloromethane, 1,2-dichloroethane and chloroform; N,N-dimethylformamide (DMF), N-methyl-2-pyrrolidone (NMP), pyridine, and the like. These solvents may be used solely or as a mixture of two or more of them.

Second Production Method

The compounds of the invention wherein various substituents are present on the group $R^5$ in the general formula (I) or the compounds wherein $R^1$ or $R^2$ is a group other than an alkoxy group can be easily synthesized by reactions obvious for those skilled in the art or modified methods thereof using the compounds of the invention as starting materials. In particular, using the compound obtained by the above first production method wherein $R^5$ is H as a starting material, the conversion of $R^5$ can be easily carried out by subjecting the compound to various reactions. For example, the following reactions can be applied.

(1) Alkylation by Nucleophilic Substitution

O-, S- or N-alkylation can be achieved by reacting a compound having OH, SH or primary to tertiary amino group with an alkylating agent such as an alkyl halide, e.g., an alkyl chloride, or an organic sulfonate ester. Alternatively, it can be also achieved by carrying out Mitsunobu reaction. The reaction is carried out in an organic solvent inert to the reaction, e.g., aromatic hydrocarbons, ethers, alcohols (methanol, ethanol, etc.), DMF, NMP, dimethyl sulfoxide (DMSO) or the like, under from cooling to heating using the compounds in equivalent amounts or one of them in excess amount. It is sometimes advantageous for smoothly progressing the reaction to carry out the reaction in the presence of a base such as sodium hydride, potassium hydride, lithium diisopropylamide, lithium hexamethyldisilazide, sodium methoxide, potassium tert-butoxide, sodium hydroxide, potassium hydroxide, sodium carbonate or potassium carbonate.

(2) Reductive Alkylation

The alkylation can be achieved by reacting a compound having a primary or secondary amine with a carbonyl compound such as a ketone or an aldehyde. A usual method for reductive alkylation can be employed in the reaction, and methods described for example in "JIKKEN KAGAKU KOZA (4th Ed.)" edited by The Chemical Society of Japan, vol. 22 (1992) (Maruzen) and the like may be mentioned.

(3) Amidation, Sulfonamidation and Esterification

Using a carboxylic acid or a sulfonic acid compound, the production can be achieved by the method of using a condensing agent in the above first production method or the method of a reactive derivative thereof. As the reactive derivative of the carboxylic acid or sulfonic acid compound, a acid halide, an acid anhydride, an active ester or the like can be employed. The reaction can be carried out by methods described for example in "JIKKEN KAGAKU KOZA (4th Ed.)" edited by The Chemical Society of Japan, vol. 22 (1992) (Maruzen) and the like.

(4) Hydrolysis

The compound of the invention having a carboxyl group can be produced by hydrolyzing a carboxylate ester compound. A usual method for hydrolysis can be employed in the reaction, and methods described for example in the deprotection of carboxyl group of "Protective Groups in Organic Synthesis (3rd Ed.)" mentioned above can be applied.

(5) Oxidation

An oxide compound such as pyridine N-oxide can be produced by oxidizing a compound having a pyridine or an amino group. As the oxidizing agent, use can be made of an inorganic oxidizing agent such as hydrogen peroxide, Oxone (trade name, Aldrich) or sodium perborate; or an organic oxidizing agent such as peracetic acid, m-chloroperbenzoic acid or dimethyldioxirane. The reaction is carried out in a solvent inert to the reaction, selected from halogenated hydrocarbons, aromatic hydrocarbons, ethers, DMF, acetic acid and water, or without solvent, under from cooling to heating. At the reaction, the oxidizing agent can be used in an equivalent amount or an excess amount relative to the starting compound. It is sometimes advantageous for smooth progress of the reaction to carry out the reaction in the presence of an inorganic acid (preferably sulfuric acid, nitric acid, hydrochloric acid or hydrobromic acid), an organic acid (preferably acetic acid or trifluoroacetic acid), or an inorganic base (preferably sodium hydroxide, potassium hydroxide or sodium hydrogen carbonate). Alternatively, a sulfinyl or sulfonyl compound can be produced by similar oxidation using a sulfanyl compound.

(6) Catalytic Reduction

The compound of the invention having an OH group can be produced by subjecting a compound having an O-benzyl group to debenzylation. For example, use can be made of a usual method for catalytic reduction wherein the reaction is carried out under a hydrogen atmosphere in the presence of palladium/carbon catalyst, and methods described in the deprotection of OH group of "Protective Groups in Organic Synthesis (3rd Ed.)" mentioned above can be also applied. Moreover, an alkenyl group can be converted into an alkyl group by the similar catalytic reduction.

Synthesis of Starting Materials

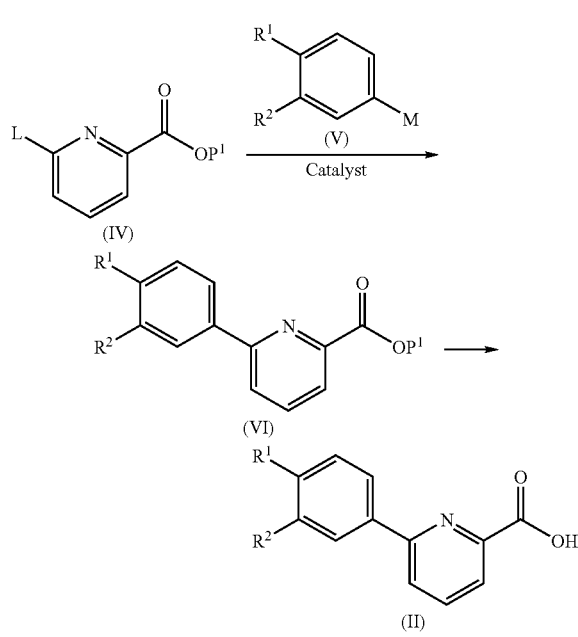

(wherein L represents a leaving group, $P^1$ represents a protective group of a carboxyl group, and M represents a metal, respectively; the same shall apply hereinafter).

The carboxylic acid compound (II) can be produced by hydrolyzing a compound (VI). The protective group of a carboxyl group in "Protective Groups in Organic Synthesis (3rd Ed.)" mentioned above can be applied to the protective group $P^1$, which can be removed by deprotection described in the literature or a usual method such as hydrolysis.

The starting compound (VI) can be produced by coupling a pyridine derivative (IV) and an arylmetal compound (V) in the presence of a catalyst. Methods described in Comprehensive Organic Synthesis, Volume 3, 481, 1991 and the like can be applied to the reaction. There may be mentioned a halogen, trifluoromethanesulfonyloxy, or the like as the leaving group L, and hydroxyboron, an alkylboron, an alkoxyboron, a magnesium halide, a zinc halide, an alkyltin, an alkylcopper, or the like as the metal M. As the catalyst, a palladium complex such as tetrakistriphenylphosphine-palladium, palladium acetate or a nickel complex such as dichlorobis(triphenylphosphine)nickel or bis(1,5-cyclooctadiene)nickel is preferable. The reaction is carried out in a solvent inert to the reaction, selected from halogenated hydrocarbons, ethers, aromatic hydrocarbons, DMF and water, or without solvent, under from cooling to heating. At the reaction, the compound (IV) and the arylmetal compound (V) can be used in an equivalent amount or one of them in excess amount, and it is sometimes advantageous for smoothly progressing the reaction to carry out the reaction in the presence of a base such as triethylamine, pyridine, 4-(N,N-dimethylamino)pyridine, sodium hydroxide, sodium carbonate, sodium hydride, sodium methoxide or potassium tert-butoxide.

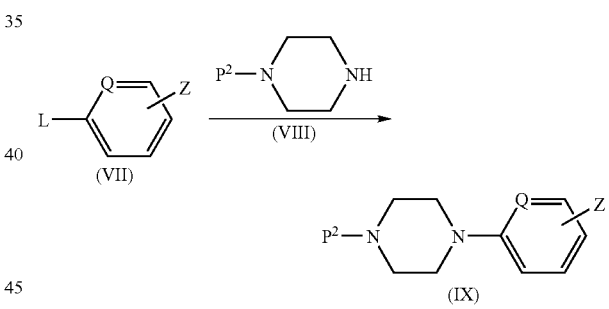

(wherein Q represents CH or N, $P^2$ represents H or a protective group of the amino group, and Z is a group selected from the G group or the like, respectively).

A starting compound (IX) can be synthesized by subjecting an aryl derivative (VII) to a coupling reaction or ipso substitution reaction with a piperazine which may be protected. The production method of the starting compound (VI) can be applied to the coupling reaction. The conditions for alkylation by the above (1) nucleophilic substitution can be applied to the ipso substitution reaction. Protective groups for an amino group described in the above "Protective Groups in Organic Synthesis (3rd Ed.)" can be applied to the protective group $p^2$ and after a reaction, the starting compound (IX) can be freed by deprotection described in the literature.

The reaction product obtained by each of the above production methods is isolated and purified as its free compound, salt or various solvates such as hydrate. The salt can be produced by carrying out a usual salt formation treatment.

The isolation and purification are carried out by employing usually used chemical techniques such as extraction, concentration, evaporation, crystallization, filtration, recrystallization and various types of chromatography.

Various isomers can be isolated in the usual way making use of the difference in physicochemical properties between corresponding isomers. For example, optical isomers can be separated by a general optical resolution method such as a fractional crystallization or chromatography. Also, an optical isomer can be produced starting from an appropriate optically active starting compound.

Furthermore, the invention also relates to a novel intermediate, a carboxylic acid derivative represented by the general formula (IIa), which is useful in the production of the phenylpyridinecarbonylpiperazine derivative (I).

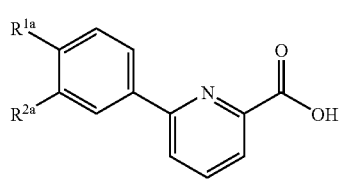

(IIa)

(wherein $R^{1a}$ represents a halogen, a lower alkyl, O-a lower alkyl, O— (a lower alkyl substituted with halogen(s)), $NH_2$, NH-a lower alkyl, N(a lower alkyl)$_2$, NHCO-a lower alkyl, O-a lower alkylene-NH-a lower alkyl, O-a lower alkylene-N(a lower alkyl)$_2$, O-a lower alkylene-$CO_2R^0$, O-a lower alkylene-a hydrocarbon ring, or O-a lower alkylene-a heterocycle, $R^{2a}$ represents H or a group described in $R^{1a}$, or $R^{1a}$ and $R^{2a}$ are combined to form —O-a lower alkylene-O—, provided that (1) when $R^{2a}$ is H, $R^{1a}$ represents a group other than methyl, ethyl, OMe, $NH_2$, NHMe or Cl, and (2) when $R^{2a}$ is methyl, $R^{1a}$ represents a group other than methyl, respectively; the same shall apply hereinafter).

The carboxylic acid compound (IIa) is included in the carboxylic acid compound (II) described in the above intermediate. The preferable groups for $R^{1a}$ and $R^{2a}$ in the compound (IIa) are the same as the preferable groups for $R^1$ and $R^2$ in the compound (I).

INDUSTRIAL APPLICABILITY

Also, the compound (I) of the invention has excellent inhibitory activity of PDE4 and is therefore useful as an agent for preventing and/or treating respiratory diseases (e.g., bronchial asthma (including atopic asthma), COPD, chronic bronchitis, pneumonic diseases and adult respiratory distress syndrome (ARDS)) in which PDE4 participates. Particularly, it can be expected to be an agent for preventing and/or treating bronchial asthma and COPD.

In addition, the compound of the invention is also useful as an agent for preventing and/or treating other diseases in which involvement of PDE4 is known, such as those in which a cytokine (IL-1, IL-4, IL-6 and TNF (tumor necrosis factor)) or the like is concerned (e.g., rheumatoid arthritis, ulcerative colitis, Crohn disease, sepsis, septic shock, endotoxin shock, Gram negative bacterial sepsis, toxic shock syndrome, nephritis, hepatitis, infection (bacterial and viral) and circulatory failure (heart failure, arteriosclerosis, myocardial infarction, stroke) or the like).

Availability of the compound (I) of the invention was confirmed by the following tests.

TEST EXAMPLE 1

PDE4 Inhibitory Activity

1) A solution containing PDE4 was purified from rat ventricle muscle in the following manner. The heart excised from a male Wistar rat under ether anesthesia was washed with physiological saline and then the ventricle was separated. The thus separated ventricle was finely cut with scissors and suspended in a buffer A (20 mM Bis-Tris, 50 mM sodium acetate, 2 mM EDTA, 5 mM 2-mercaptoethanol, 2 mM benzamidene, 0.05 mM phenyl-methyl-sulfonyl fluoride, pH 6.5) containing 1% Protease Inhibitor Cocktail For Mammalian Cell Extracts (SIGMA). Thereafter, the cells were disrupted using Polytron and subjected to ultracentrifugation (100,000 G, 60 minutes, 4° C.) to obtain a soluble fraction.

2) The resulting soluble fraction was charged to a 2.6×10 cm Q-Sepharose column equilibrated with the buffer A. Next, the column was washed with 1,200 ml of the buffer A to remove uncombined protein. The protein combined to the column was eluted using 750 ml of the buffer A containing a linear gradient sodium acetate solution of from 0.05 to 1.00 M, and 110 tubes each containing 7 ml fraction were recovered. The cAMP metabolizing PDE activity of each fraction obtained in the presence or absence of cGMP and calcium/calmodulin was investigated. Each fraction which showed cAMP metabolizing activity and received no influence on the cAMP metabolizing activity by the presence of cGMP or calcium/calmodulin was used as a stock solution for the inspection of PDE4 inhibitory activity.

3) Each test compound in a desired concentration was allowed to undergo 10 minutes of the reaction at 30° C. in a reaction mixture containing 40 mM Tris-HCl (pH 8.0), 5 mM magnesium chloride, 4 mM 2-mercaptoethanol, 1 μM cAMP, 1 μCi/ml [$^3$H]cAMP and the PDE4 stock solution. The reaction was stopped by adding ½ volume of 20 mg/ml polylysine coated yttrium silicate SPA beads (Amersham) suspension containing 18 mM zinc sulfate and 5 μM 3-isobutyl-1-methylxanthine (IBMX) to the reaction solution, and the radioactivity was measured.

A concentration of test compound which inhibits 50% of the metabolic activity of PDE4 was defined as $IC_{50}$ and calculated for each compound. By applying the above test method and the method described in WO 97/19078, inhibitory activity against PDE1, PDE2, PDE3 and PDE5 was measured similarly.

As a result of the above measurement, it was revealed that the compounds of Examples 2, 10, 15, 32, 43, 45, 77, 95, 99 and 112 have an $IC_{50}$ value of 12 nM or less for PDE4. Moreover, in the same concentration, they hardly exhibited inhibitory activity against PDE1, PDE2, PDE3 and PDE5. Accordingly, it was confirmed that the compound of the invention is a strong and selective PDE4 inhibitor.

TEST EXAMPLE 2

Oral Absorbability and Pharmacokinetic Profile Evaluation Test Using TNF-A Production Inhibitory Activity as the Index 1) Each test compound suspended in purified water containing 0.5% methyl cellulose was orally administered to a eight-week-old male Fisher rat at a dose of 10 mg/kg. In the control group, a solvent (0.5% methyl cellulose in purified water, 3 ml/kg) was administered in the same manner. After the oral administration, blood samples were periodically collected in the presence of heparin from the caudal vein of each rat under ether anesthesia, and plasma was prepared in the usual way.

2) The plasma prepared above (final concentration 2.5%), RPMI1640 medium containing 10% bovine fetal serum, 20 µl of whole blood of male Wister rat and LPS (final concentration 3 µg/ml) were dispensed to a 96-well culture plate so that the total volume per 1 well was 200 µl, followed by culturing at 37° C. using a $CO_2$ incubator overnight. After the completion of the culturing, the plate was centrifuged (1,500 r.p.m., 10 minutes), the supernatant was recovered, and the amount of TNF-A in the supernatant was measured using a commercially available ELISA kit.

As a result of this test, it was revealed that the compound of the invention has good oral absorbability.

Based on the results of the above inhibitory activity measuring tests, it was confirmed that the compound (I) of the invention exhibits selective and potent inhibitory activity against PDE4 as well as good oral absorbability, and thus it is evident that it is useful as an agent for preventing and treating diseases in which PDE4 participates.

TEST EXAMPLE 3

Action on Antigen-induced Eosinophile Infiltration in Rat Airway

An OA solution for sensitization (final concentration: OA; 1 mg/ml, $Al(OH)_3$; 20 mg/ml) was administered intraperitoneally to a four-week-old Brown Norway female rat (Charles River Japan, Inc., Kanagawa) continuously for 3 days at a dose of 1 ml per rat to effect antigen-sensitization. The first day of administration was assigned to be Day 0. On Day 21 or 22, 1% OA/physiological saline was atomized by means of an ultrasonic nebulizer (NE-U12, Omron) and the sensitized rat was exposed to the antigen by letting the rat inhale the atomized OA for 20 minutes to induce infiltration of eosinophiles into airway. In addition, a group wherein physiological saline was inhaled for exposure was used as a normal control group. A test compound was suspended in a 0.5% MC aqueous solution and the suspension was administered orally 1 hour before the antigen inhalation and exposure. The animal was under fasting state from the day before the antigen inhalation and exposure and, after the antigen inhalation and exposure, it was released from the fasting state. After 24 hours from the antigen inhalation and exposure, the animal was subjected to laparotomy under Nembutal anesthesia and was exsanguinated from aorta abdominalis to death. Thereafter, a cannula (6 Fr-Atom venous catheter, Atom) was inserted to the airway, and bronchoalveolar lavage (PAT) was carried out by repeating the operation of injecting and recovering 2 ml of physiological saline containing heparin (1 unit/ml) five times (10 ml in total). After the recovered BAL liquid was centrifuged at 500×g (4° C., 10 minutes), the supernatant was removed and the precipitate (cell fraction) was re-suspended with 500 µl of physiological saline containing heparin (1 unit/ml). Total leukocyte concentration in the re-suspended liquid was measured by means of a hemocyte-counting apparatus (celltac-α, Nihon Kohden Corporation) and then a spread specimen was prepared and stained with a blood-staining liquid for differentiation (Dif Quick, International Reagents Corporation), then observed under the microscope to calculate the abundance ratio of eosinophiles from the morphological characteristic. Based on the total number of leukocytes and the eosinophile abundance ratio, total number of eosinophiles was calculated and thereby the effect of the drug was evaluated.

TEST EXAMPLE 4

Action on LPS-induced Neutrophile Infiltration in Rat Airway

Infiltration of neutrophiles into the airway was induced by administering, within the airway by means of 200 µl sonde, a 10 µg/ml LPS (lipopolysaccharide E. coli 0127:B8 Boivin, DIFCO) solution dissolved in physiological saline to a six-week-old Wister male rat (Charles River Japan, Inc., Kanagawa) anesthetized by administering an appropriate amount of a ketamine/xylazine mixed solution intraperitoneally. In addition, a group wherein physiological saline was administered within the airway was used as a normal control group. A test compound was suspended in a 0.5% MC aqueous solution and the suspension was administered orally 1 hour before the LPS administration within the airway. The animal was under fasting state from the day before the LPS administration within the airway and, after the LPS administration within the airway, it was released from the fasting state. After 24 hours from the LPS administration within the airway, the animal was subjected to laparotomy under Nembutal anesthesia and was exsanguinated from aorta abdominalis to death. Thereafter, total leukocyte concentration was measured in a similar manner to the above Test Example 3. Furthermore, the abundance ratio of neutrophiles was similarly calculated from the morphological characteristic observed under the microscope. Based on the total number of leukocytes and the neutrophile abundance ratio, total number of neutrophiles was calculated and thereby the effect of the drug was evaluated.

The pharmaceutical preparation containing one or two or more of the compounds of the invention or salts thereof as the active ingredient is prepared using carriers, excipients and other additives which are generally used in the preparation of medicaments.

The administration may be either oral administration in the form of, e.g., tablets, pills, capsules, granules, powders or liquids or parenteral administration in the form of, e.g., intravenous or intramuscular injections, suppositories, transdermal preparations, transnasal preparations or inhalations. The dose is optionally decided in response to each case, e.g., by taking symptoms, age and sex of each patient to be treated into consideration, but is usually approximately from 0.001 mg/kg to 100 mg/kg per day per adult in the case of oral administration, which is administered once a day or by dividing into 2 to 4 doses per day. Also, when intravenous administration is conducted due to the symptoms, it is administered once or several times a day generally within the range of from 0.0001 mg/kg to 10 mg/kg per day per adult. Also, in the case of inhalation, it is administered once or several times a day generally within the range of from 0.0001 mg/kg to 1 mg/kg per day per adult.

The solid composition for the oral administration according to the invention is used in the form of, e.g., tablets, powders or granules. In such a solid composition, one or more active substances are mixed with at least one inert excipient such as lactose, mannitol, glucose, hydroxypropylcellulose, microcrystalline cellulose, starch, polyvinylpyrrolidone or aluminum magnesium metasilicate. In the usual way, the composition may contain inert additives including a lubricant such as magnesium stearate and a disintegrating agent such as carboxymethylstarch sodium or a solubilization assisting agent. If necessary, tablets or pills may be coated with a film of sugar or a gastric or enteric coating agent.

The liquid composition for oral administration contains, e.g., pharmaceutically acceptable emulsions, liquids, suspensions, syrups and elixirs and contains a generally used inert solvent such as purified water or ethanol. In addition to the inert solvent, this composition may also contain auxiliary agents such as a solubilizing agent, a moistening agent and a suspending agent, as well as sweeteners, flavors, aromatics and antiseptics.

The injections for parenteral administration include aseptic aqueous or non-aqueous liquids, suspensions and emulsions. Examples of the aqueous solvent include distilled water for injection and physiological saline. Examples of the non-aqueous solvent include propylene glycol, polyethylene glycol, a plant oil such as olive oil, an alcohol such as ethanol, and polysorbate 80 (trade name). Such a composition may further contain a tonicity agent, an antiseptic, a moistening agent, an emulsifying agent, a dispersing agent, a stabilizing agent and a solubilization assisting agent. These compositions are sterilized, e.g., by filtration through a bacteria-retaining filter, blending of a germicide or irradiation. In addition, these may be used by firstly making into sterile solid compositions and dissolving them in sterile water or a sterile solvent for injection prior to their use.

The transmucomembranous preparations such as inhalations and transnasal preparations are used in the form of solid, liquid or semi-solid, and may be produced in accordance with hitherto known methods. For example, an excipient such as lactose or starch and further a pH regulating agent, an antiseptic, a surfactant, a lubricant, a stabilizing agent, and a thickening agent may be optionally added thereto. For the administration, an appropriate device for inhalation or blowing can be used. For example, using a known device such as a metered dose-inhaling device or a nebulizer, the compound may be administered solely or as a powder of formulated mixture, or as a solution or suspension in combination with a pharmaceutically acceptable carrier. A dry powder-inhaling device or the like may be a device for single use or a device for several uses, where a dry power or a capsule containing a power can be utilized. Alternatively, it may be in the form of a pressurized aerosol spray wherein an appropriate propellant, e.g., a suitable gas such as chlorofluoroalkane, hydrofluoroalkane or carbon dioxide is employed.

BEST MODE FOR CARRYING OUT THE INVENTION

The invention will be specifically described below with reference to Examples which, however, do not limit the scope of the invention. Methods for producing the starting compounds are shown in Reference Examples.

REFERENCE EXAMPLE 1

To a mixture of methyl 6-chloropyridine-2-carboxylate, 3,4-dimethoxyphenylboric acid, dimethoxyethane and water were added palladium acetate, triphenylphosphine and sodium carbonate, and they were reacted at 100° C. for 1 hour to obtain methyl 6-(3,4-dimethoxyphenyl)pyridine-2-carboxylate. Thus obtained compound was reacted at 60° C. for 30 minutes in a mixed solution of THF-methanol with adding a 1M aqueous sodium hydroxide solution, whereby 6-(3,4-dimethoxyphenyl)pyridine-2-carboxylic acid was obtained.

REFERENCE EXAMPLE 2

To a THF solution of 4-bromo-2-chloroanisole was added an n-butyllithium/n-hexane solution at −78° C., followed by 30 minutes of stirring. Then, trimethyl borate was added and the whole was warmed to room temperature, followed by 30 minutes of stirring. Using the residue obtained by evaporation of the solvent instead of 3,4-dimethoxyphenylboric acid, an objective compound was obtained in a similar manner to Reference Example 1.

REFERENCE EXAMPLE 3

Using 1-benzyloxy-4-bromo-2-methoxybenzene, an objective compound was obtained in a similar manner to Reference Example 2 with the exception that the hydrolysis was carried out in a 1M aqueous sodium hydroxide solution at 100° C. for 2.5 days.

REFERENCE EXAMPLE 4

Using 6-(3,4-dimethoxyphenyl)pyridine-2-carboxylic acid and t-butoxycarbonylpiperazine, 1-{[6-(3,4-dimethoxyphenyl)pyridine-2-carbonyl]-4-(t-butoxycarbonyl) piperazine was obtained in a similar manner to Example 2 to be mentioned below. Further, a 4M hydrogen chloride/ethyl acetate solution was added thereto and the whole was reacted to obtain an objective compound.

REFERENCE EXAMPLE 5

Using 1-benzyloxycarbonyl-4-(t-butoxycarbonyl)-piperazine-2-carboxylic acid and morpholine, 1-benzyloxycarbonyl-4-(t-butoxycarbonyl)-2-[(morpholin-4-yl)carbonyl]piperazine was obtained in a similar manner to Example 4 to be mentioned below. In ethyl acetate, a 4M hydrogen chloride/ethyl acetate solution was added thereto and the whole was reacted to obtain 1-benzyloxycarbonyl-2-[(morpholin-4-yl)carbonyl]piperazine. The compound was heated to reflux for 1 day in toluene in the presence of bromobenzene, tris (dibenzylideneacetone)dipalladium(0), 2,2'-bis(diphenylphosphino)-1,1'-binaphthyl and sodium t-butoxide to obtain 1-benzyloxycarbonyl-2-morpholinocarbonyl-4-phenylpiperazine. Further, thus obtained compound was stirred at room temperature for 1.5 days in ethanol in the presence of 10% palladium/carbon under a hydrogen atmosphere of normal pressure. After filtration of insoluble matter, the residue obtained by evaporation of the solvent was dissolved in ethanol, 10% palladium/carbon and ammonium formate were added thereto, and the whole was stirred at an oil bath temperature of 70° C. for 2.5 days to obtain an objective compound.

REFERENCE EXAMPLE 6

To a DMF solution of 4-bromo-2-ethylphenol were added potassium carbonate and benzyl bromide, and the whole was stirred at an oil bath temperature of 60° C. for 30 minutes to obtain benzyl (4-bromo-2-ethylphenyl) ether, which was then treated in a similar manner to the first half of Reference Example 2 to obtain methyl 6-(4-benzyloxy-3-ethylphenyl) pyridine-2-carboxylate. The obtained compound was stirred in a mixed solution of methanol and THF in the presence of 10% palladium/carbon under a hydrogen atmosphere of normal pressure at room temperature for 24 hours and then thus obtained product was dissolved in trifluoroacetic acid. Pentamethylbenzene was added thereto under ice cooling and the whole was stirred at an oil bath temperature of 50° C. for 1 hour and further at room temperature for 4.5 days to obtain methyl 6-(3-ethyl-4-hydroxyphenyl)pyridine-2-carboxylate. The obtained compound was treated with trifluoromethanesulfonic anhydride in pyridine to obtain methyl 6-(3-ethyl-4-trifluoromethanesulfonyloxyphenyl)pyridine-2-carboxylate. Further, to a 1,4-dioxane solution of the ester compound obtained above were added tributylvinyltin, lithium chloride, tetrakis(triphenylphosphine)palladium(0), and 2,6-di-t-butyl-4-methylphenol, and the whole was heated to reflux for 18 hours. Thereafter, tetrakis(triphenylphosphine)palladium(0) was further added thereto, followed by 2 days of heating under reflux. Then, potassium fluoride was added thereto at room temperature and the whole was stirred at room temperature for 2 days to obtain methyl 6-(3-ethyl-4-vinylphenyl)pyridine-2-carboxylate. The compound was treated with a 1M aqueous sodium hydroxide solution in methanol to obtain an objective compound.

REFERENCE EXAMPLE 7

To a DMF solution of methyl 6-(3-ethyl-4-hydroxyphenyl)pyridine-2-carboxylate were added potassium carbonate and methyl iodide, and the whole was stirred at an oil bath temperature of 70° C. for 2 hours to obtain methyl 6-(3-ethyl-4-methoxyphenyl)pyridine-2-carboxylate, which was then stirred in methanol and a 1M aqueous sodium hydroxide solution at an oil bath temperature of 60° C. for 1 hour to obtain an objective compound.

REFERENCE EXAMPLE 8

4-Iodophenol was reacted with 2-chlorodimethylamioethane hydrochloride in DMF under heating in the presence of potassium carbonate to obtain [2-(4-iodophenoxy)ethyl]dimethylamine. The obtained compound was reacted in toluene under heating in the presence of t-butyl piperazine-1-carboxylate, sodium t-butoxide, tri(2-methylphenyl)phosphine and a catalytic amount of tris(dibenzylideneacetone)dipalladium(0) to obtain an objective compound.

REFERENCE EXAMPLE 9

2,6-Dichloropyridine was reacted with t-butyl piperazine-1-carboxylate in N,N-dimethylimidazolidinone under heating in the presence of potassium carbonate to obtain an objective compound.

REFERENCE EXAMPLE 10

In a mixed solvent of THF-methanol, methyl 6-(3-benzyloxy-4-methoxyphenyl)pyridine-2-carboxylate was stirred in the presence of palladium/carbon under a hydrogen atmosphere to obtain methyl 6-(3-hydroxy-4-methoxyphenyl)pyridine-2-carboxylate. The obtained compound is reacted with cyclopropylmethyl bromide and potassium carbonate in DMF under heating to obtain methyl 6-(3-cyclopropylmethoxy-4-methoxyphenyl) pyridine-2-carboxylate, which was further reacted in a mixed solvent of THF-methanol under heating with adding a 1M aqueous sodium hydroxide solution to obtain an objective compound.

REFERENCE EXAMPLE 11

To a toluene solution of 4-bromo-2-chloroanisole were added 1-(t-butoxycarbonyl)-piperazine, tris(dibenzylideneacetone)dipalladium(0), 2,2'-bis(diphenylphosphino)-1,1'-binaphthyl and sodium t-butoxide, followed by 4 hours of heating at an oil bath temperature of 110° C. Then, post-treatment and purification were carried out in a usual way to obtain an objective compound.

REFERENCE EXAMPLE 12

Trifluoroacetic acid was added to a chloroform solution of 1-(t-butoxycarbonyl)-4-(3-chloro-4-methoxyphenyl)piperazine and the whole was stirred for 30 minutes. Then, post-treatment and purification were carried out in a usual way to obtain an objective compound.

REFERENCE EXAMPLE 13

An NMP solution of 6-chloronicotinonitrile and (±)-trans-2,5-dimethylpiperazine was stirred at an oil bath temperature of 120° C. for 1 hour to obtain an objective compound.

REFERENCE EXAMPLE 14

Potassium carbonate was added to an NMP solution of 4-fluorobenzaldehyde and 1-(t-butoxycarbonyl)piperazine, and the whole was stirred under heating. Then, post-treatment and purification were carried out in a usual way to obtain an objective compound.

REFERENCE EXAMPLE 15

To piperazine melted at 150° C. was added 2-chlorobenzothiazole, followed by 1 hour of stirring. Then, post-treatment and purification were carried out in a usual way to obtain an objective compound.

REFERENCE EXAMPLE 16

To a mixture of 60% sodium hydride and THF were added dropwise ethyl diethylphosphonoacetate and further 4-[4-(t-butoxycarbonyl)piperazin-1-yl]benzaldehyde under cooling to 0° C., followed by stirring. Then, post-treatment and purification were carried out in a usual way to obtain ethyl 3-{4-[4-(t-butoxycarbonyl)piperazin-1-yl]phenyl}acrylate. Further, catalytic reduction was carried out using palladium/carbon to obtain an objective compound.

REFERENCE EXAMPLE 17

A DMSO solution of methyl 6-chloro-nicotinate and piperazine was stirred at an oil bath temperature of 120° C. to obtain an objective compound.

REFERENCE EXAMPLE 18

Palladium/carbon was added to a methanol-THF mixed solution of 1-(3-benzyloxy-4-nitrophenyl)-4-(t-butoxycarbonyl)piperazine, followed by stirring under a hydrogen atmosphere. Methyl orthoformate and p-toluenesulfonic acid were added to a methanol solution of 2-amino-5-[1-(t-butoxycarbonyl)piperazin-4-yl]phenol obtained by post-treatment and purification in a usual way, followed by heating under stirring. Then, post-treatment and purification were carried out in a usual way to obtain an objective compound.

REFERENCE EXAMPLE 19

N-Benzyliminodiacetic acid was reacted with CDI and 5-aminoindole in THF to obtain 4-benzyl-1-(1H-indol-5-yl)piperazine-2,6-dione, which was then reacted with lithium aluminum hydride in THF. Conc. hydrochloric acid and palladium hydroxide were added to an ethanol solution of thus obtained compound and the whole was reacted under a hydrogen atmosphere of 3 atm for 65 hours to obtain an objective compound.

REFERENCE EXAMPLE 20

4-(2-Chloropyrimidin-4-yl)piperazine-1-carbaldehyde and 2-(dimethylamino)ethanol were reacted in DMF in the presence of potassium t-butoxide. Thus obtained compound was reacted in methanol in the presence of potassium carbonate at 80° C. for 24 hours to obtain an objective compound.

REFERENCE EXAMPLE 21

4-[4-(t-Butoxycarbonyl)piperazin-1-yl]benzaldehyde and [3-(ethoxycarbonyl)propyl]triphenylphosphonium bromide were reacted in THF in the presence of potassium t-butoxide to obtain ethyl 5-{4-[4-(t-butoxycarbonyl)piperazin-1-yl]phenyl}-4-pentenoate, which was then subjected to catalytic reduction using palladium/carbon to obtain an objective compound.

REFERENCE EXAMPLE 22

2-Bromo-6-iodopyridin-3-ol was reacted with potassium carbonate and benzyl bromide to obtain 3-(benzyloxy)-2-bromo-6-iodopyridine, which was then reacted in a similar manner to Reference Example 11, Example 22 and Example 4, successively. Further, the resulting product was subjected to catalytic reduction using palladium/carbon to obtain an objective compound.

REFERENCE EXAMPLE 23

To a DMF solution of 2-bromo-6-{4-[6-(3,4-dimethoxyphenyl)pyridine-2-carbonyl]piperazin-1-yl}pyridin-3-ol were added 60% sodium hydride and ethyl 4-bromobutanoate, followed by 1 hour of reaction at room temperature. Then, post-treatment and purification were carried out in a usual way to obtain an objective compound.

REFERENCE EXAMPLE 24

4-(2-Chloropyrimidin-4-yl)piperazine-1-carbaldehyde and benzyl alcohol were treated in a similar manner to Reference Example 20 and Example 4, successively. Then, the resulting product was subjected to catalytic reduction using palladium/carbon and further treated in a similar manner to Reference Example 23 to obtain an objective compound.

REFERENCE EXAMPLE 25

To 4-[6-(3,4-dimethoxyphenyl)pyridine-2-carbonyl]-1-(4-hydroxyphenyl)piperazine were added 1,2-dibromoethane, a 2M aqueous sodium hydroxide solution, tetra-n-butylammonium hydrogen sulfate and water, followed by stirring at 60° C. After cooling of the reaction solution, water and chloroform were added thereto, insoluble matter was removed by filtration, and then the resulting product was subjected to post-treatment and purification in a usual way to obtain an objective compound.

REFERENCE EXAMPLE 26

Potassium t-butoxide was added to a DMF solution of 2,5-dibromopyridine and 2-(dimethylamino)ethanol, and the whole was stirred at an oil bath temperature of 100° C. for 3 hours to obtain N-{2-[(5-bromopyridin-2-yl)oxy]ethyl}—N,N-dimethylamine, which was further treated in a similar manner to Reference Examples 11 and 12 to obtain an objective compound.

REFERENCE EXAMPLE 27

2-(Benzyloxy)-6-bromonaphthalene was treated in a similar manner to Reference Example 11, Example 22 and Example 4, successively, to obtain 1-[6-(benzyloxy)-2-naphthyl]-4-[6-(3,4-dimethoxyphenyl) pyridine-2-carbonyl]piperazine. The compound was dissolved in trifluoroacetic acid, pentamethylbenzene was added thereto under ice cooling, and the whole was stirred at room temperature for 2 hours and further at an oil bath temperature of 40° C. for 2 hours to obtain an objective compound.

REFERENCE EXAMPLE 28

To an acetonitrile solution of (±)-trans-4-(2,5-dimethylpiperazin-1-yl)benzaldehyde were added di(t-butoxycarbonyl) dicarbonate and 4-dimethylaminopyridine, followed by stirring. Then, post-treatment and purification were carried out in a usual way to obtain an objective compound.

REFERENCE EXAMPLE 29

An NMP solution of fluoro-4-nitrobenzene and (±)-trans-2,5-dimethylpiperazine was stirred at an oil bath temperature of 120° C. for 3 hours to obtain (±)-trans-2,5-dimethyl-1-(4-nitrophenyl)piperazine, which was further treated in a similar manner to Example 4 to obtain an objective compound.

REFERENCE EXAMPLE 30

Methyl 3-oxobutyrate was added to an acetic anhydride solution of 6-chloroquinoline 1-oxide, followed by 30 minutes of stirring at an oil bath temperature of 40° C. Thus obtained compound was added to 10% hydrochloric acid and the mixture was reacted at room temperature to obtain methyl (6-chloroquinolin-2-yl)acetate. The compound was further treated in a similar manner to Reference Example 11, Example 22 and Example 4, successively, to obtain an objective compound.

In a similar manner to the above Reference Examples or the following Examples, the compounds of Reference Examples 31 to 69 shown in the following Tables 1 to 5 were obtained, respectively. Structures and physicochemical data of the compounds of Reference Examples 1 to 69 are shown in Tables 1 to 5.

EXAMPLE 1

To a THF (20 ml) solution of 740 mg of 2-oxo-3-phenylpiperazine was added 638 mg of lithium aluminum hydride, followed by 3 hours of heating under reflux. The reaction solution was cooled with ice and sodium sulfate decahydrate was added until gel disappeared in the reaction solution. After stirring for a while, insoluble matter was removed by filtration. Crude 2-phenylpiperazine obtained by evaporation of the solvent was added to a THF (20 ml) solution of 500 mg of 6-(3,4-dimethoxyphenyl)pyridine-2-carboxylic acid, and 556 mg of WSC hydrochloride and 260 mg of HOBt were further added thereto, followed by 2 days of stirring at room temperature. Ethyl acetate was added to the reaction solution and the mixture was washed with water and brine. After drying over anhydrous magnesium sulfate, the solvent was evaporated. The obtained residue was purified by silica gel column chromatography (chloroform-methanol) to obtain colorless amorphous crystals (670 mg). The compound was dissolved in ethanol and 192 mg of fumaric acid was added thereto to form its fumarate salt, which was then recrystallized from ethanol-ethyl acetate to obtain 607 mg of 2-(3,4-dimethoxyphenyl)-6-(3-phenylpiperazine-1-carbonyl)pyridine 0.5 fumarate as colorless crystals.

EXAMPLE 2

To a THF (20 ml) solution of 500 mg of 6-(3,4-dimethoxyphenyl)pyridine-2-carboxylic acid were added 0.18 ml of oxalyl chloride and one drop of DMF under ice cooling. After 30 minutes of stirring, the reaction solution was added dropwise to a pyridine (10 ml) solution of 370 mg of 4-(4-methoxyphenyl)piperazine under ice cooling. The mixture was warmed to room temperature and further stirred for 30 minutes. Water was added to the reaction solution, followed by extraction with ethyl acetate. The organic layer was washed with brine and dried over anhydrous magnesium sulfate, and then the solvent was evaporated. The residue was purified by silica gel column chromatography (chloroform-methanol) and recrystallization was further carried out from ethyl acetate-acetonitrile to obtain 370 mg of 1-[6-(3,4-dimethoxyphenyl)pyridine-2-carbonyl]-4-(4-methoxyphenyl)piperazine as colorless crystals.

EXAMPLE 3

In 15 ml of a 4M hydrogen cloride/ethylacetate solution, 0.62 g of t-butyl 4-[4-(2-dimethylaminoethoxy)phenyl]piperazine-1-carboxylate was reacted. To a DMF (15 ml) solution of 0.86 g of a crude product obtained by evaporation of the solvent were added 0.34 g of WSC hydrochloride, 0.24 g of HOBt and 0.41 g of 6-(3,4-dimethoxyphenyl)pyridine-2-carboxylic acid, followed by 65 hours of reaction at room temperature. Further, 0.34 g of WSC hydrochloride, 0.24 g of HOBt and 0.50 ml of triethylamine were added thereto, followed by 8.5 hours of stirring at room temperature. Water was added to the reaction solution, followed by extraction with ethyl acetate. The organic layer was washed with water and brine and dried over anhydrous magnesium sulfate, and then the solvent was evaporated. The residue was purified by silica gel column chromatography (ethyl acetate) and then thus obtained compound was subjected to salt formation with 106 mg of oxalic acid. Recrystallization (ethanol) was carried out to obtain 253 mg of 1-[6-(3,4-dimethoxyphenyl)pyridine-2-carbonyl]-4-[4-(2-dimethylaminoethoxy)phenyl]piperazine dioxalate as pale yellow crystals.

EXAMPLE 4

To a THF (20 ml) solution of 500 mg of 6-(3,4-dimethoxyphenyl)pyridine-2-carboxylic acid and 500 mg of 1-(5-chlorothiazol-2-yl)piperazine were added 400 mg of WSC hydrochloride, 320 mg of HOBt and 0.3 ml of triethylamine at room temperature. After 4 hours of stirring, water was added thereto, followed by extraction with ethyl acetate. The organic layer was washed with water and brine and dried over anhydrous magnesium sulfate. After the solvent was evaporated, the residue was purified by silica gel column chromatography (chloroform-methanol) and recrystallization was further carried out from diisopropyl ether-acetonitrile to obtain 560 mg of 1-(5-chlorothiazol-2-yl)-4-[(6-3,4-dimethoxyphenyl)pyridine-2-carbonyl]piperazine as colorless crystals.

EXAMPLE 5

To a THF solution of ethyl 4-[N-(4-{4-[6-(3,4-dimethoxyphenyl)pyridine-2-carbonyl]piperazin-1-yl}phenyl)amino]butanoate were added a 36% aqueous formalin solution, acetic acid and sodium triacetoxyborohydride, followed by stirring. Then, post-treatment and purification were carried out in a usual way to obtain ethyl 4-[N-(4-{4-[6-(3,4-dimethoxyphenyl)pyridine-2-carbonyl]piperazin-1-yl}phenyl)-N-methylamino]butanoate.

EXAMPLE 6

To a THF (5 ml) and methanol (5 ml) mixed solution of 1.01 g of ethyl 3-(4-{4-[6-(3,4-dimethoxyphenyl)pyridine-2-carbonyl]piperazin-1-yl }phenyl)propanoate was added 5 ml of a 1M aqueous sodium hydroxide solution, followed by 1 hour of stirring at room temperature. To the reaction solution was added 5 ml of a 1M aqueous hydrochloric acid solution, followed by extraction with ethyl acetate. The organic layer was washed with brine and dried over anhydrous magnesium sulfate. After the solvent was evaporated, thus obtained crude crystals were recrystallized from ethanol to obtain 673 mg of 3-(4-{4-[6-(3,4-dimethoxyphenyl)pyridine-2-carbonyl]piperazin-1-yl}phenyl) propanoic acid as colorless crystals.

EXAMPLE 7

In 15 ml of a 4M hydrochloric acid-ethyl acetate solution, 0.71 g of 2-chloro-6-(4-t-butoxycarbonylpiperazin-1-yl) pyrazine was stirred at room temperature for 7 hours. The solvent was evaporated to obtain a crude product of 2-chloro-6-(piperazin-1-yl)pyrazine hydrochloride. The obtained crude product and 0.62 g of 6-(3,4-dimethoxyphenyl)pyridine-2-carboxylic acid were treated in a similar manner to Example 4 to obtain 594 mg of 2-chloro-6-{4-[6-(3,4-dimethoxyphenyl)pyridine-2-carbonyl]piperazin-1-yl}pyrazine as pale yellow crystals.

EXAMPLE 8

To a dichloromethane (10 ml) solution of 353 mg of 1-[6-(3,4-dimethoxyphenyl)pyridine-2-carbonyl]-4-(pyridin-4-yl)piperazine was added 195 mg of m-chloroperbenzoic acid, followed by 1 hour of stirring at 50C. An aqueous sodium thiosulfate solution was added to the reaction solution, followed by extraction with chloroform. The organic layer was washed with water and brine and then dried over anhydrous magnesium sulfate, and thereafter, the solvent was evaporated. The residue was purified by silica gel column chromatography (chloroform-methanol) and then recrystallization (ethanol-ethyl acetate) was carried out to obtain 294 mg of 1-[6-(3,4-dimethoxyphenyl)pyridine-2-carbonyl]-4-(1-oxidopyridin-4-yl) piperazine 1.5 hydrate as pale yellow crystals.

EXAMPLE 9

To an ethanol (70 ml) and water (25 ml) mixed solution of 2.5 g of 1-[6-(3,4-dimethoxyphenyl)pyridine-2-carbonyl]-4-(4-nitrophenyl)piperazine were added 0.15 g of ammonium chloride and 3.1 g of reduced iron, followed by 2 hours of heating under reflux. The reaction solution was filtered through celite and the filtrate was concentrated under reduced pressure. An aqueous sodium hydrogen carbonate solution was added to thus obtained residue, followed by extraction with chloroform. The organic layer was washed with brine and then dried over anhydrous magnesium sulfate, and thereafter, the solvent was evaporated. The residue was purified by silica gel column chromatography (chloroform-methanol) and further, crystallization was carried out from acetonitrile-ethyl acetate to obtain 2.1 g of 1-[6-(3,4-dimethoxyphenyl)pyridine-2-carbonyl]-4-(4-aminophenyl)piperazine as pale pink crystals.

EXAMPLE 10

To a DMF (10 ml) solution of 1.50 g of 4-{4-[6-(3,4-dimethoxyphenyl)pyridine-2-carbonyl]piperazin-1-yl}phenol were added 1.00 g of 4-chloromethylpyridine-N-oxide and 3.00 g of cesium carbonate, followed by 30 minutes of stirring at room temperature. After warmed to 60° C., the mixture was further stirred for 30 minutes. Then, 1.00 g of 4-chloromethylpyridine-N-oxide and 1.50 g of cesium carbonate were added thereto and the whole was stirred at 60° C. for 1 hour. After cooling to room temperature, water was added thereto, followed by extraction with ethyl acetate. The organic layer was washed with water and brine and then dried over anhydrous magnesium sulfate, and thereafter, the solvent was evaporated. The residue was purified by silica gel column chromatography (chloroform-methanol) and then recrystallization was carried out from ethanol to obtain 440 mg of 1-[6-(3,4-dimethoxyphenyl)pyridine-2-carbonyl]-4-[4-(1-oxido-4-pyridylmethoxy)phenyl]piperazine as pale yellow crystals.

EXAMPLE 11

To an ethanol (6 ml) solution of 327 mg of 1-[6-(3,4-dimethoxyphenyl)pyridine-2-carbonyl]piperazine monohydrochloride were added 0.28 ml of triethylamine and 148 mg of 2,4-dichloropyrimidine, followed by 2 hours of stirring at an oil bath temperature of 90° C. After the solvent was evaporated, water was added thereto, followed by extraction with chloroform. The organic layer was washed with water and then dried over anhydrous magnesium sulfate, and thereafter, the solvent was evaporated. The residue was purified by silica gel column chromatography (hexane-ethyl acetate) and further, recrystallization was carried out from acetonitrile-diisopropyl ether to obtain 70 mg of 2-chloro-4-{4-[6-(3,4-dimethoxyphenyl)pyridine-2-carbonyl]piperazin-1-yl}pyrimidine monohydrate as colorless crystals.

EXAMPLE 12

To a THF (5 ml) solution of 171 mg of 4-{4-[6-(3,4-dimethoxyphenyl)pyridine-2-carbonyl]piperazin-1-yl}benzoic acid was added 63 mg of CDI, followed by stirring at 60° C. Further, 52 mg of CDI was added in twice thereto, and the whole was stirred at 60° C. for 24 hours in total. After the reaction solution was cooled to room temperature, 0.25 ml of aqueous ammonia was added thereto, followed by 6 hours of stirring at room temperature. Further, 0.5 ml of aqueous ammonia was added thereto and the whole was stirred at room temperature. Thus precipitated crude crystals were collected by filtration and recrystallized from methanol-THF to obtain 68 mg of 4-{4-[6-(3,4-dimethoxyphenyl)pyridine-2-carbonyl]piperazin-1-yl}benzamide as colorless crystals.

EXAMPLE 13

To an ethanol (8 ml) and THF (8ml) mixed solution of 159 mg of benzyl 4-(4-{4-[6-(3,4-dimethoxyphenyl)pyridine-2-carbonyl]piperazin-1-yl) phenylcarbamoyl}piperidine-1-carboxylate was added 18 mg of 10% palladium/carbon under an argon atmosphere. After 2 hours of stirring at room temperature under a hydrogen atmosphere of normal pressure, the mixture was filtered through celite and the filtrate was concentrated under reduced pressure. The residue was purified by silica gel column chromatography (chloroform-methanol-aqueous ammonia) and then recrystallization was carried out from acetonitrile to obtain 70 mg of 4'-{4-[6-(3,4-dimethoxyphenyl)pyridine-2-carbonyl]piperazin-1-yl}piperidine-4-carboxyanilide as colorless crystals.

EXAMPLE 14

To a chloroform (5 ml) solution of 1.20 g of 1-(benzofuran-5-yl)-4-(t-butoxycarbonyl)piperazine was added 5 ml of trifluoroacetic acid at 0° C., and the whole was warmed to room temperature, followed by 1 hour of stirring. After neutralization with a 1M aqueous sodium hydroxide solution, extraction with chloroform was carried out. The organic layer was washed with brine. After drying over anhydrous magnesium sulfate, the solvent was evaporated. Using a 500 mg portion of 910 mg of 1-(benzofuran-5-yl)piperazine thus obtained, 420 mg of 1-(benzofuran-5-yl)-4-[6-(3,4-dimethoxyphenyl)pyridine-2-carbonyl]piperazine was obtained as colorless crystals.

EXAMPLE 15

To a DMF (3 ml) solution of 355 mg of 1-(4-aminophenyl)-4-[6-(3,4-dimethoxyphenyl)pyridine-2-carbonyl]piperazine were added 130 mg of 1-chloro-2-(2-chloroethoxy)ethane, 77 mg of sodium iodide and 249 mg of potassium carbonate, followed by overnight stirring at 100° C. After cooled to room temperature, the reaction solution was concentrated under reduced pressure and then water was added thereto, followed by extraction with chloroform. The organic layer was washed with brine and then dried over anhydrous magnesium sulfate, and thereafter, the solvent was evaporated. The residue was purified by silica gel column chromatography (chloroform-methanol) and then crystallization was carried out from ethanol-diethyl ether to obtain 210 mg of 4-(4-{4-[6-(3,4-dimethoxyphenyl)pyridine-2-carbonyl]piperazin-1-yl)phenyl)morpholine as yellow crystals.

EXAMPLE 16

To a THF (2.5 ml) solution of 211 mg of 1-(4-aminophenyl)-4-[6-(3,4-dimethoxyphenyl)pyridine-2-carbonyl]piperazine were added 63.5 mg of methanesulfonyl chloride and 76.8 μl of triethylamine, followed by overnight stirring at room temperature. Further, 79 mg of methanesulfonyl chloride and 103 μl of triethylamine were added in twice thereto, and the whole was stirred at room temperature for 3 hours. Water was added to the reaction solution, followed by extraction with ethyl acetate. The organic layer was washed with brine and then dried over anhydrous magnesium sulfate, and thereafter, the solvent was evaporated. The residue was purified by silica gel column chromatography (chloroform-methanol) and then crystallization was carried out from ethyl acetate-diisopropyl ether to obtain 175 mg of 4'-{4-[6-(3,4-dimethoxyphenyl)pyridine-2-carbonyl]piperazin-1-yl}methanesulfonanilide as pale purple crystals.

EXAMPLE 17

To 233 mg of ethyl [(4-{4-[6-(3,4-dimethoxyphenyl)pyridine-2-carbonyl]piperazin-1-yl}benzoyl)amino]acetate was added 0.8 ml of conc. hydrochloric acid, followed by overnight stirring at room temperature. After the reaction solution was concentrated under reduced pressure, crystallization was carried out from 2-propanol-diisopropyl ether to collect [(4-f4-[6-(3,4-dimethoxyphenyl)pyridine-2-carbonyl]piperazin-1-yl}benzoyl)amino]acetic acid hydrochloride by filtration. The filtrate was concentrated under reduced pressure, and the residue was crystallized from hexane to obtain 88 mg of [(4-{4-[6-(3,4-dimethoxyphenyl)pyridine-2-carbonyl]piperazin-1-yl}benzoyl)amino]acetic acid hydrate as pale brown crystals.

EXAMPLE 18

To an NMP (7.5 ml) solution of 1.51 g of 2,5-dichloropyrazine were added 2.00 g of 1-(t-butoxycarbonyl)piperazine and 2.00 g of potassium carbonate, followed by 1 hour of stirring under heating at 100° C. The mixture was cooled to room temperature, and water was added thereto, followed by extraction with ethyl acetate. The organic layer was washed with water and brine and then dried over anhydrous magnesium sulfate, and thereafter, the solvent was evaporated. The residue was purified by silica gel column chromatography (chloroform-methanol) to obtain 2.73 g of 2-chloro-5-(4-t-butoxycarbonylpiperazin-1-yl)pyrazine. Using this compound, 2-chloro-5-{4-[6-(3,4-dimethoxyphenyl)pyridine-2-carbonyl]piperazin-1-yl}pyrazine was obtained in a similar manner to Example 14 as colorless crystals.

EXAMPLE 19

To a methanol (20 ml) solution of 460 mg of 2-chloro-4-{4-[6-(3,4-dimethoxyphenyl) pyridine-2-carbonyl]piperazin-1-yl}pyrimidine monohydrate was added 150 mg of 10% palladium/carbon, followed by 23 hours of stirring at room temperature under a hydrogen atmosphere of normal pressure. Insoluble matter was removed by filtration and the residue obtained by evaporation of the solvent was purified by silica gel column chromatography (chloroform-methanol) and further, recrystallization was carried out from acetonitrile-diisopropyl ether to obtain 83 mg of 4-{4-[6-(3,4-dimethoxyphenyl)pyridine-2-carbonyl]piperazin-1-yl}pyrimidine as colorless crystals.

EXAMPLE 20

To 297 mg of 4-[6-(3,4-dimethoxyphenyl)pyridine-2-carbonyl]-1-(4-hydroxyphenyl)piperazine were added 623 mg of [1,3]dioxolan-2-one and 147 mg of potassium carbonate, followed by 1.5 hours of stirring at 100° C. After the mixture was cooled to room temperature, water and then 1M hydrochloric acid were added to the reaction solution, which was then neutralized with a saturated aqueous sodium hydrogen carbonate solution, followed by extraction with chloroform. The organic layer was washed with brine and then dried over anhydrous magnesium sulfate, and thereafter, the solvent was evaporated. The residue was purified by silica gel column chromatography (chloroform-methanol) and then recrystallization was carried out from ethyl acetate to obtain 41 mg of 2-(4-{4-[6-(3,4-dimethoxyphenyl)pyridine-2-carbonyl]piperazin-1-yl}phenoxy)ethanol as pale yellow crystals.

EXAMPLE 21

To a DMF (5 ml) solution of 213 mg of 6-{4-[6-(3,4-dimethoxyphenyl)pyridine-2-carbonyl]piperazin-1-yl}pyridin-3-ol were added 81 mg of (2-chloroethyl)dimethylamine hydrochloride and 43 mg of 60% sodium hydride under ice cooling. After 1 hour of stirring at an oil bath temperature of 70° C., water was added thereto, followed by extraction with ethyl acetate. The organic layer was washed with brine and then dried over anhydrous magnesium sulfate, and thereafter, the solvent was evaporated. The residue was purified by silica gel column chromatography (chloroform to chloroform-methanol) and thus obtained product (110 mg) was dissolved in ethanol and converted into its oxalate salt by adding 40 mg of oxalic acid. Thereafter, the salt was recrystallized from ethanol to obtain 81 mg of 1-[6-(3,4-dimethoxyphenyl)pyridine-2-carbonyl]-4-[5-(2-dimethylaminoethoxy)-2-pyridyl]piperazine oxalate as colorless crystals.

EXAMPLE 22

To a chloroform (3 ml) solution of t-butyl 4-[2-(4-{4-[6-(3,4-dimethoxyphenyl)pyridine-2-carbonyl]piperazin-1-yl}phenoxy)ethyl]piperazine-1-carboxylate was added 0.427 ml of a 4M hydrogen chloride/ethyl acetate solution, followed by 2 days of stirring at room temperature. Further, 2 ml of chloroform and 1 ml of a 4M hydrogen chloride/ethyl acetate solution were added thereto, and the whole was stirred at room temperature overnight. Ethanol was added to the reaction mixture and crude crystals were collected by filtration and recrystallized from methanol to obtain 114 mg of 1-[6-(3,4-dimethoxyphenyl)pyridine-2-carbonyl]-4-[4-(2-piperazin-1-ylethoxy)phenyl]piperazine tetrahydrochloride hydrate as pale yellow crystals.

EXAMPLE 23

To an ethanol (37 ml) and water (13 ml) mixed solution of 1.42 g of (±)-trans-1-[6-(3,4-dimethoxyphenyl)pyridine-2-carbonyl]-2,5-dimethyl-4-(4-nitrophenyl)piperazine were added 0.16 g of ammonium chloride and 1.66 g of reduced iron, followed by 0.5 hour of heating under reflux. The reaction solution was filtered through celite and the filtrate was concentrated under reduced pressure. An aqueous saturated sodium hydrogen carbonate solution was added to thus obtained residue, followed by extraction with chloroform. The organic layer was washed with brine and then dried over anhydrous magnesium sulfate, and thereafter, the solvent was evaporated. The residue was purified by silica gel column chromatography (chloroform-methanol) and the obtained compound was treated with a 4M hydrogen chloride/ethyl acetate solution to form its salt. Then, the solvent was evaporated and the residue was washed with ethyl acetate to obtain 582 mg of (±)-trans-4-{4-[6-(3,4- dimethoxyphenyl)pyridine-2-carbonyl]-2,5-dimethylpiperazin-1-yl}aniline hydrochloride hydrate as pale yellow crystals.

In a similar manner to the above Examples, the compounds of Examples 24 to 115 shown in the following Tables 6 to 8 were obtained, respectively. Structures and physicochemical data of the compounds of Examples 1 to 115 are shown in Tables 6 to 8.

EXAMPLES 116 to 147

To a DMF (0.7 ml) solution of 13 mg (0.05 mmol) of 6-(3,4-dimethoxyphenyl)pyridine-2-carboxylic acid were added a DMF (0.06 ml) solution of each of various amine (0.06 mmol) and 25 mg of diisopropylethylamine. Then, a DMF (0.3 ml) solution of 23 mg of 2-(1H-benzotriazol-1-yl)-1,1,3,13-tetramethyluronium hexafluorophosphate was added thereto, followed by 24 hours of stirring at room temperature. PS-isocyanate (1.55 mmol/g, 100 mg; Argonaut) was added and the whole was stirred at room temperature for 14 hours. The reaction solution was filtered, and 3 ml of chloroform and 3 ml of a 1M aqueous sodium hydroxide solution were added to the filtrate, followed by stirring. The chloroform layer was dried over anhydrous sodium sulfate and then the solvent was evaporated to obtain each compound of Examples 116 to 147 shown in the following Table 9. Structure and physicochemical data of individual compounds are shown in Table 9.

Furthermore, structures of the other compounds of the invention are shown in Tables 10 to 13. These can be easily synthesized using the above production methods, the methods described in Examples and methods obvious for those skilled in the art, or modified methods thereof.

The following abbreviations are used in the following Tables. REx: Reference Example number, Ex: Example number, No: Compound number, Dat: physicochemical data (F: FAB-MS $(M+H)^+$, FN: FAB-MS $(M-H)^-$, EI: EI-MS $(M^+)$, MP: melting point (° C.), NMR1: δ (ppm) of characteristic peaks of $^1$H-NMR in CDCl$_3$, NMR2: δ (ppm) of characteristic peaks of $^1$H-NMR in DMSO-d$_6$, Sal: salt and contained solvent (Ox: oxalate, Fum: fumarate, blank column: free compound, the numeral before a component, for example, 2 HCl means dihydrochloride), Syn: production method (each numeral indicates a similarly produced Example number or Reference Example number), Me: methyl, Et: ethyl, cPr: cyclopropyl, tBu: t-butyl, Ph: phenyl, Bn: benzyl, Ac: acetyl, Pip: piperidin-1-yl, Pip4: piperidin-4-yl, Mor: morpholin-4-yl, Pipr: piperazin-1-yl and Pyrr: pyrrolidin-1-yl. In addition, the numeral before each substituent shows the position of substitution, for example, 2-Cl means 2-chloro, 3,4-diMe means 3,4-dimethyl, 2,3,4-triMe means 2,3,4-trimethyl, 4-Me-Pipr means 4-methylpiperazin-1-yl and 3,4-(OCH$_2$O) means 3,4-methylenedioxy group, respectively.

TABLE 1

| REx | Syn | P$^2$ | R$^3$ | R$^4$ | R$^5$ | Dat |
|---|---|---|---|---|---|---|
| 5 | — | H | morpholin-N-CO— | H | Ph | F: 276 |
| 13 | — | H | Me | Me | 6-methyl-3-cyanopyridin-yl | F: 217 |
| 28 | — | Boc | Me | Me | 4-CHO-Ph | F: 319 |
| 31 | REx16 | Boc | Me | Me | 4-(CH$_2$)$_2$CO$_2$Et-Ph | EI: 390 |
| 32 | REx21 | Boc | Me | Me | 4-(CH$_2$)$_4$CO$_2$Et-Ph | FN: 417 |
| 33 | REx12 | H | Me | Me | 4-(CH$_2$)$_2$CO$_2$Et-Ph | F: 291 |

TABLE 1-continued

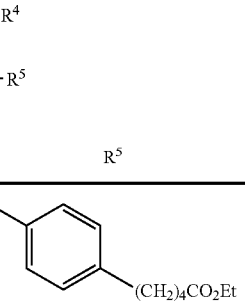

| REx | Syn | P² | R³ | R⁴ | R⁵ | Dat |
|---|---|---|---|---|---|---|
| 34 | REx12 | H | Me | Me | 4-methylphenyl-(CH₂)₄CO₂Et | F: 319 |
| 35 | REx13 | H | Me | Me | 4-CHO-Ph | F: 219 |
| 36 | REx13 | H | Me | Me | 4-Ac-Ph | F: 233 |

TABLE 2

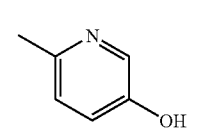

| REx | Syn | R¹ | R² | Dat |
|---|---|---|---|---|
| 1 | — | MeO | MeO | NMR2: 8.18(1H, d, J=8.0 Hz), 7.09(1H, d, J=8.0Hz), 3.87(3H, s); F: 260 |
| 2 | — | MeO | Cl | FN: 262 |
| 3 | — | BnO | MeO | F: 336 |
| 6 | — | CH₂=CH— | Et | F: 254 |
| 7 | — | MeO | Et | F: 258 |
| 10 | — | MeO | cPr—CH₂O | FN: 294 |
| 37 | REx2 | MeO | F | FN: 246 |
| 38 | REx2 | MeO | BnO | NMR1: 6.95–7.05(1H, m), 5.28(2H, s), 3.95(3H, s) |
| 39 | REx10 | MeO | CF₂H—O | NMR1: 7.93–8.00(2H, m), 7.01(1H, d, J=8.0Hz), 1.35–1.42(1H, m) |

TABLE 3

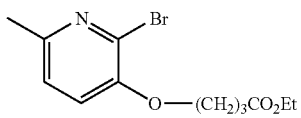

| REx | Syn | R³ | R⁴ | R⁵ | Dat |
|---|---|---|---|---|---|
| 4 | — | H | H | H | F: 328 |
| 22 | — | H | H | 6-methyl-3-hydroxypyridin-yl | F: 421 |
| 23 | — | H | H | 6-methyl-2-bromo-3-(O—(CH₂)₃CO₂Et)pyridin-yl | F: 535 |

TABLE 3-continued
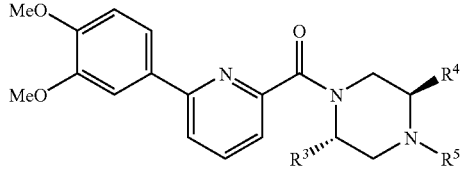
| REx | Syn | R³ | R⁴ | R⁵ | Dat |
|---|---|---|---|---|---|
| 24 | — | H | H | 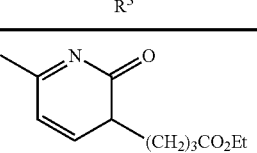 | F: 536 |
| 25 | — | H | H | 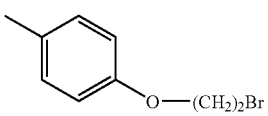 | F: 526 |
| 27 | — | H | H | 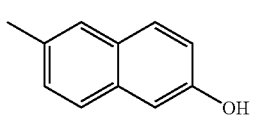 | F: 470 |
| 29 | — | Me | Me | 4-NO₂-Ph | F: 477 |
| 30 | — | H | H | 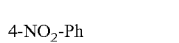 | F: 527 |
| 40 | REx25 | H | H | 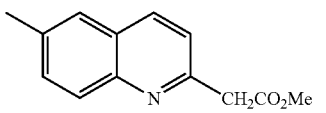 | F: 506 |
| 41 | REx25 | H | H | 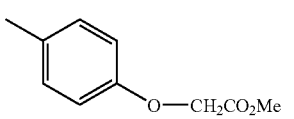 | F: 534 |
| 42 | REx25 | H | H | 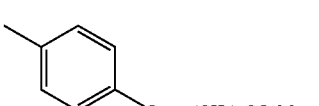 | F: 576 |
| 43 | REx25 | H | H | 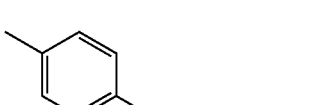 | F: 534 |
| 44 | REx25 | H | H | 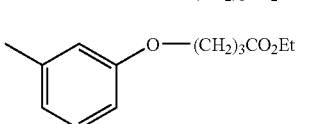 | F: 534 |
| 45 | REx25 | H | H | 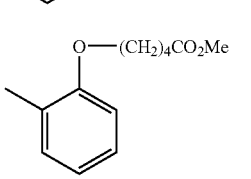 | F: 632 |

TABLE 3-continued

| REx | Syn | R³ | R⁴ | R⁵ | Dat |
|---|---|---|---|---|---|
| 46 | REx25 | H | H | 4-Me-Ph-NH-(CH₂)₃CO₂Et | F: 533 |
| 47 | Ex5 | H | H | 4-Me-Ph-NH-C(O)-piperidine-N-CO₂-Bn | F: 664 |
| 48 | Ex5 | Me | Me | 4-Me-Ph-(CH₂)₂CO₂Et | F: 532 |
| 49 | Ex5 | Me | Me | 4-Me-Ph-(CH₂)₄CO₂Et | F: 560 |
| 50 | REx12 & Ex5 | H | H | 4-Me-Ph-(CH₂)₂CO₂Et | NMR1: 6.97(1H, d, J=8.4 Hz), 4.12(2H, q, J=7.2 Hz), 2.89(2H, t, J=7.6Hz) |
| 51 | REx12 & Ex5 | H | H | 6-Me-pyridin-3-yl-(CH₂)₂CO₂Et | NMR1: 6.97(1H, d, J=8.8 Hz), 4.12(2H, q, J=7.2 Hz), 2.84(2H, t, J=7.6Hz) |

TABLE 4

| REx | Syn | R⁵ | Dat |
|---|---|---|---|
| 8 | — | 4-Me-Ph-O-(CH₂)₂-NMe₂ | F: 350 |
| 9 | — | 6-Me-2-Cl-pyrimidin-4-yl | F: 299 |
| 11 | — | 3-Cl-4-OMe-Ph | NMR1: 6.99(1H, d, J=2.8Hz), 3.85(3H, s), 1.48(9H, s) |
| 14 | — | 4-CHO-Ph | NMR1: 9.80(1H, s), 3.37–3.40 (4H, m), 1.49(9H, s) |

TABLE 4-continued

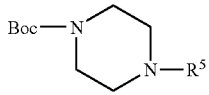

| REx | Syn | R⁵ | Dat |
|---|---|---|---|
| 16 | — | 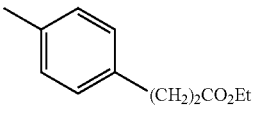 4-(CH₂)₂CO₂Et-Ph | NMR1: 4.12(2H, q, J=7.2Hz), 2.87(2H, t, J=7.6Hz), 1.48(9H, s) |
| 18 | — | 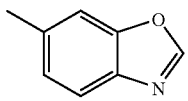 benzoxazol-6-yl | NMR1: 7.97(1H, s), 3.15–3.19 (4H, m), 1.49(9H, s) |
| 21 | — | 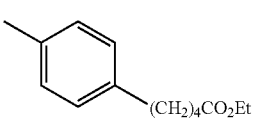 4-(CH₂)₄CO₂Et-Ph | NMR1: 4.12(2H, q, J=7.2Hz), 2.31(2H, t, J=7.2Hz), 1.48(9H, s) |
| 52 | REx11 | 3-F-4-OMe-Ph | NMR1: 6.72(1H, dd, J=14, 2.8Hz), 3.85(3H, s), 1.48(9H, s) |
| 53 | REx11 | 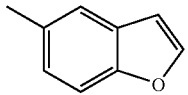 benzofuran-5-yl | NMR1: 7.58(1H, d, J=2.4Hz), 3.07–3.09(4H, m), 1.49(9H, s) |
| 54 | REx11 | 4-(NEt₂)-Ph | F: 334 |
| 55 | REx14 | 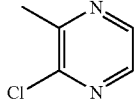 3-Cl-pyrazin-2-yl | NMR1: 7.91(1H, d, J=2.4Hz), 3.58–3.61(4H, m), 1.49(9H, s) |
| 56 | REx14 | 2-Cl-4-Ac-Ph | NMR1: 7.07(1H, d, J=8.8Hz), 3.08–3.12(4H, m), 1.49(9H, s) |
| 57 | REx14 | 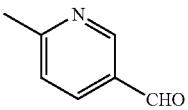 6-Me-5-CHO-pyridin-2-yl | NMR1: 9.80(1H, s), 3.54–3.58 (4H, m), 1.49(9H, s) |
| 58 | REx16 | 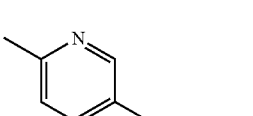 6-(CH₂)₂CO₂Et-pyridin-2-yl | NMR1: 6.60(1H, d, J=8.8Hz), 4.12(2H, q, J=7.2Hz), 2.56 (2H, t, J=7.6Hz) |
| 59 | REx10 & REx14 | 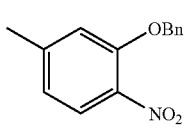 3-OBn-4-NO₂-Ph | NMR1: 8.01(1H, d, J=8.4Hz), 5.22(2H, s), 1.49(9H, s) |

TABLE 5

| REx | Syn | R⁵ | Dat |
|---|---|---|---|
| 12 | — | 3-Cl-4-OMe-Ph | F: 227 |
| 15 | — | 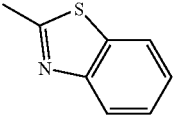 benzothiazol-2-yl | F: 220 |

TABLE 5-continued

| REx | Syn | R⁵ | Dat |
|---|---|---|---|
| 17 | — | 6-methyl-pyridin-3-yl-CO₂Me | F: 222 |
| 19 | — | 5-methyl-1H-indole | EI: 201 |
| 20 | — | 4-methyl-2-(2-(dimethylamino)ethoxy)pyrimidine | F: 252 |
| 26 | — | 5-methyl-2-(2-(dimethylamino)ethoxy)pyridine | F: 251 |
| 60 | REx12 | 3-F-4-OMe-Ph | F: 211 |
| 61 | REx12 | 3-methyl-2-chloropyrazine | NMR2: 8.26(1H, d, J=2.4Hz), 7.97(1H, d, J=2.4Hz), 2.81–2.84 (4H, m) |
| 62 | REx12 | 4-(NEt₂)-Ph | F: 234 |
| 63 | REx11 & REx12 | 3-methyl-5-methoxypyridine | NMR1: 7.96(1H, d, J=2.4Hz), 7.82(1H, d, J=2.4Hz), 3.84(3H, s) |
| 64 | REx11 & REx12 | 6-methylquinoline | EI: 213 |
| 65 | REx11 & REx12 | 6-methyl-2-bromopyridine | F: 242 |
| 66 | REx13 | 3-CF₃-4-Ac-Ph | F: 273 |
| 67 | REx13 | 3-OH-4-Ac-Ph | F: 221 |
| 68 | REx13 | 6-methyl-3-nitropyridine | F: 209 |
| 69 | REx13 & REx12 | 4-methyl-6-chloropyrimidine | F: 199 |

TABLE 6
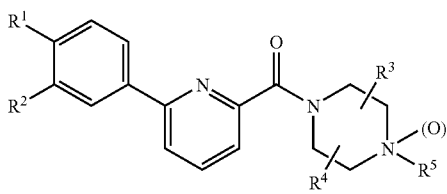
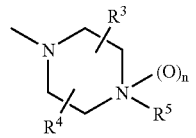
| Ex | Syn | | Dat | Sal |
|---|---|---|---|---|
| 1 | — | 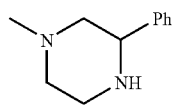 | NMR2: 7.63–7.73(2H, m), 4.52 (1H, m), 2.77–3.33(4H, m); MP: 180–181 | 0.5 Fum |
| 23 | | 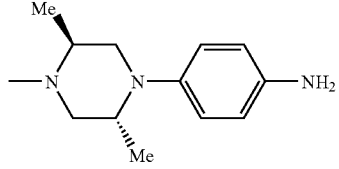 | NMR2: 8.09–7.93(2H, m), 7.76–7.64(2H, m), 1.02(3H, d, J=6.3 Hz); MP 205–210 | HCl H$_2$O |
| 24 | Ex4 | 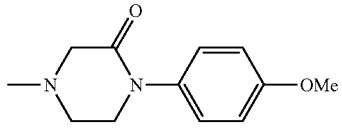 | NMR2: 7.08(1H, dd, J =8.3, 3.0 Hz), 6.98–6.94(2H, m), 4.08–4.01 (1H, m); MP: 147–148 | |
| 25 | Ex1 | 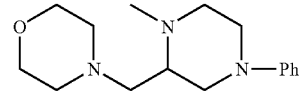 | NMR2: 7.93(1H, t, J=7.8Hz), 3.86 (3H, s), 2.09(1H, m) MP: 173–176(dec.) | Fum |
| 26 | Ex3 | 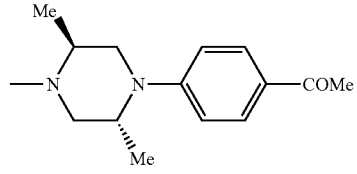 | NMR2: 1.10–1.13(3H, m), 1.31–1.37(3H, m), 2.44(3H, s); MP: 134–135 | |
| 27 | Ex6 | 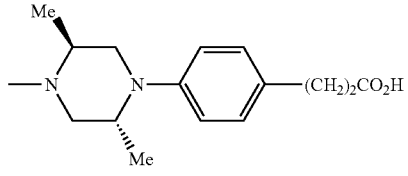 | NMR2: 0.96–0.99(3H, m), 3.82–3.84(6H, m), 7.05–7.11(2H, m); MP: 160–162 | |
| 28 | Ex6 | 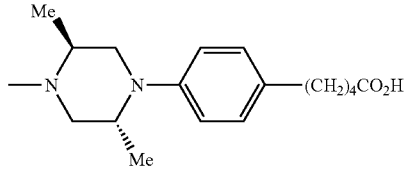 | NMR2: 0.95–0.98(3H, m), 1.93–1.96(2H, m), 3.81–3.84(6H, m); MP: 124–127 | 3 H$_2$O |

TABLE 6-continued
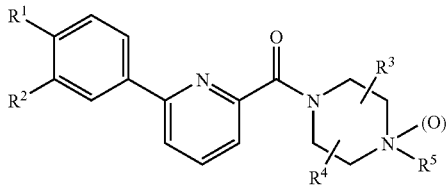
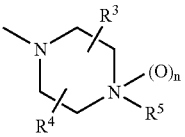
| Ex | Syn | R⁴ R⁵ | Dat | Sal |
|---|---|---|---|---|
| 29 | Ex4 | 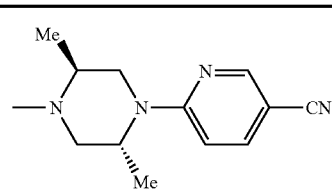 | NMR2: 8.50(1H, d, J=2.0Hz), 3.83(3H, s), 3.82(3H, s), 1.33–1.14 (6H, m); MP: 93–99 | |
| 30 | Ex15 | 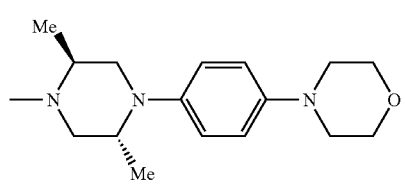 | NMR1: 7.87–7.66(3H, m), 3.06–3.03(4H, m), 1.12–1.04(3H, m); MP: 167–172 | |
| 31 | Ex8 | 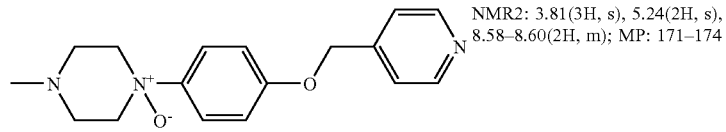 | NMR2: 3.81(3H, s), 5.24(2H, s), 8.58–8.60(2H, m); MP: 171–174 | |
TABLE 7
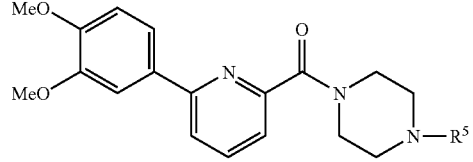
| Ex | Syn | R⁵ | Dat | Sal |
|---|---|---|---|---|
| 2 | — | 4-OMe-Ph | NMR1: 7.84(1H, t, J=7.8Hz), 3.96 (3H, s), 3.78(2H, s); MP: 169–172 | |
| 3 | — | 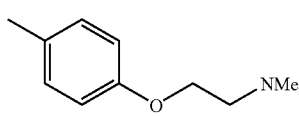 | NMR2: 3.85(3H, s), 3.82(3H, s), 3.13–3.16(4H, m), 2.79(6H, s); MP: 136–137 | 2 Ox |
| 4 | — | 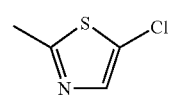 | NMR1: 7.01(1H, m), 6.98(1H, d, J=8.3Hz), 3.56–3.61(4H, m); MP: 141–143 | |
| 5 | — | 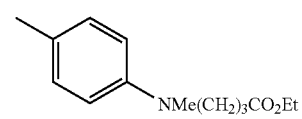 | F: 547 | |

TABLE 7-continued
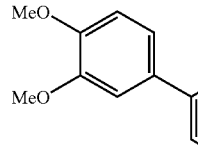
| Ex | Syn | R⁵ | Dat | Sal |
|---|---|---|---|---|
| 6 | — | 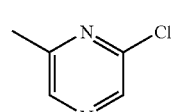 (CH₂)₂CO₂H | NMR2: 12.06(1H, s), 7.53(1H, d, J=7.4Hz), 2.73(2H, t, J=7.6Hz); MP: 169–171 | |
| 7 | — | 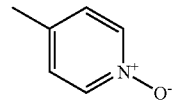 | NMR2: 8.32(1H, s), 7.90(1H, s), 3.88 (3H, s), 3.83(3H, s); MP: 160–161 | |
| 8 | — | 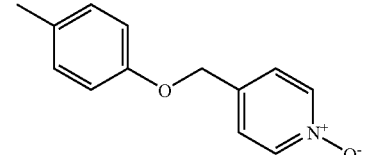 | NMR2: 8.28–8.30(2H, m), 3.87(3H, s), 3.83(3H, s); F: 421 | 1.5 H₂O |
| 9 | — | 4-NH₂-Ph | NMR2: 4.62(2H, br s), 3.85(3H, s), 2.98–3.03(4H, m); Mp: 164–165 | |
| 10 | — | 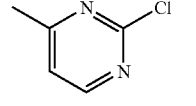 | NMR2: 3.82(3H, s), 5.05(2H, s), 8.19–8.23(2H, m); MP: 182–183 | |
| 11 | — | 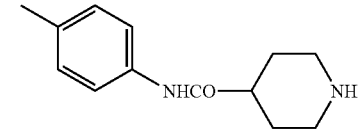 | NMR1: 8.10(1H, d, J=6.3Hz), 6.98 (1H, d, J=8.7Hz), 6.43(1H, d, J=6.3 Hz); MP: 98–100 | H₂O |
| 12 | — | 4-CONH₂-Ph | NMR2: 3.85(3H, s), 7.03(1H, br s), 7.68–7.79(5H, m); MP: 237–240 | |
| 13 | — | 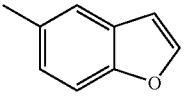 | NMR2: 1.44–1.54(2H, m), 3.85(3H, s), 9.59(1H, s); MP: 217–219 | |
| 14 | — | 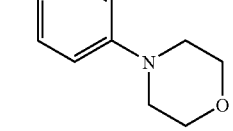 | NMR1: 6.97(1H, d, J=8.3Hz), 6.69–6.71 (1H, m), 3.20–3.30(4H, m); MP: 176–178 | |
| 15 | — | 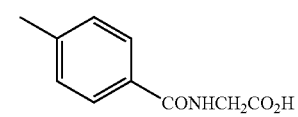 | NMR2: 3.69–3.73(6H, m), 3.85(3H, s), 6.85–6.91(4H, m); MP: 129–130 | |
| 16 | — | 4-(NHSO₂Me)-Ph | NMR2: 2.88(3H, s), 3.82(3H, s), 9.28(1H, s); MP: 168–170 | |
| 17 | — |  CONHCH₂CO₂H | NMR2: 3.82(3H, s), 8.55(1H, t, J=5.8Hz), 12.50(1H, br s); MP: 114–117 | H₂O |

TABLE 7-continued

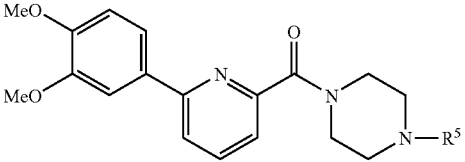

| Ex | Syn | R⁵ | Dat | Sal |
|---|---|---|---|---|
| 18 | — | 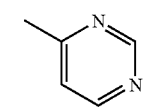 | NMR1: 8.11(1H, d, J=1.5Hz), 6.98 (1H, d, J=8.3Hz), 3.69–3.80(4H, m); MP: 160–162 | |
| 19 | — | 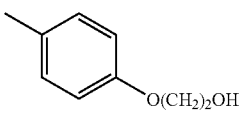 | NMR1: 8.63(1H, s), 8.26(1H, d, J=6.3Hz), 6.98(1H, d, J=8.3Hz); MP: 138–139 | |
| 20 | — | 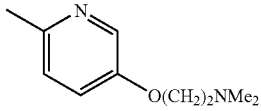 | NMR2: 3.65–3.72(4H, m), 3.82(3H, s), 4.80(1H, t, J=5.4Hz); MP: 111–113 | |
| 21 | — | 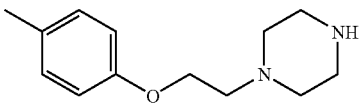 | NMR1: 6.66(1H, d, J=8.8Hz), 3.97 (3H, s), 3.95(3H, s), 2.91(6H, s); MP: 144–147 | Ox |
| 22 | — | 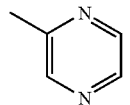 | NMR2: 3.82(3H, s), 3.84(3H, s), 7.68–7.72(2H, m) MP: 155–158 | 4 HCl H₂O |
| 32 | Ex2 | 4-Ac-Ph | NMR1: 7.78(1H, dd, J=8.3, 1.0Hz), 3.96(3H, s), 2.53(3H, s); MP: 161–163 | |
| 33 | Ex2 | 4-NMe₂-Ph | NMR2: 3.85(3H, s), 3.82(3H, s), 3.05–3.08(4H, m), 2.79(6H, s); MP: 159–161 | |
| 34 | Ex4 | 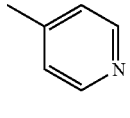 | NMR2: 8.36(1H, d, J=0.9Hz), 7.09 (1H, d, J=8.0Hz), 3.86(3H, s), 3.82 (3H, s); MP: 122–124 | |
| 35 | Ex4 | 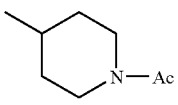 | NMR2: 8.19(2H, d, J=5.9Hz), 3.86 (3H, s), 3.82(3H, s), 3.45–3.52(4H, m); MP: 155–156 | |
| 36 | Ex4 | 2-Cl-4-OMe-Ph | NMR2: 7.15(1H, d, J=9.0Hz), 7.05 (1H, d, J=3.0Hz), 6.91(1H, dd, J= 9.0, 3.0Hz); MP: 155–156 | |
| 37 | Ex4 | 4-CN-Ph | NMR2: 8.06(1H, d, J=7.8Hz), 3.85 (3H, s), 3.47–3.54(4H, m); MP: 146–148 | |
| 38 | Ex4 | 4-CO₂Et-Ph | NMR2: 3.86(3H, s), 3.45–3.51(4H, m), 1.29(3H, t, J=7.3Hz); MP: 112–114 | |
| 39 | Ex5 | —CH₂-(2-OH-3-OMe-Ph) | NMR1: 7.54(1H, dd, J=8.3, 2.0Hz), 3.78(2H, s), 2.76–2.66(4H, m); MP: 155–158 | |
| 40 | Ex5 |  | NMR1: 6.97(1H, d, J=8.3Hz), 3.98 (3H, s), 2.09(3H, s); MP: 120–122 | |

TABLE 7-continued

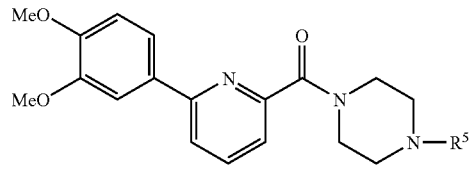

| Ex | Syn | R⁵ | Dat | Sal |
|---|---|---|---|---|
| 41 | Ex4 & Ex7 | 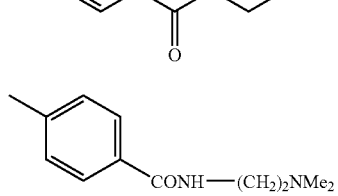 | NMR2: 3.86(3H, s), 3.83(3H, s), 2.75(3H, d, J=4.4Hz); F: 530 | 2 HCl 2 H₂O |
| 42 | Ex4 & Ex7 | 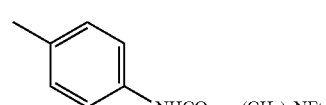 | NMR2: 8.67(1H, t, d=5.4Hz), 3.86 (3H, s), 3.83(3H, s), 2.82(3H, s), 2.80(3H, s); F: 518 | 2 HCl 2 H₂O |
| 43 | Ex3 | 4-NHAc-Ph | NMR2: 1.99(3H, s), 3.85(3H, s), 9.71(1H, s); MP: 201–203 | |
| 44 | Ex3 | 4-(NHCO-Ph)-Ph | NMR2: 3.82(3H, s), 6.98(2H, d, J=9.3Hz), 10.07(1H, s); MP: 169–171 | |
| 45 | Ex4 | 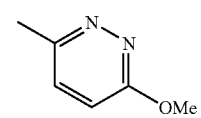 | NMR2: 1.19(6H, t, J=7.4Hz), 2.72–2.75(2H, m), 10.02(1H, s); MP: 131–134 | Ox |
| 46 | Ex6 | 4-CO₂H-Ph | NMR2: 3.86(3H, s), 6.99(2H, d, J=9.3Hz), 12.32(1H, br s); MP: 209–211 | |
| 47 | Ex4 | 4-OH-Ph | NMR2: 3.84(3H, s), 6.82(2H, d, J=8.8Hz), 8.88(1H, s); MP: 177–179 | |
| 48 | Ex4 | 4-NO₂-Ph | NMR2: 3.86(3H, s), 7.04(2H, d, J=9.2Hz), 8.06–8.10(3H, m); MP: 142–144 | |
| 49 | Ex4 | 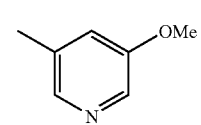 | NMR1: 7.05(1H, d, J=9.8Hz), 6.98 (1H, d, J=8.3Hz), 6.89(1H, d, J=9.3 Hz), 4.04(3H, s); MP: 171–172 | |
| 50 | Ex4 | 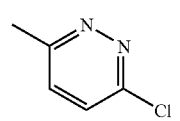 | NMR1: 7.58(1H, dd, J=8.3, 2.0Hz), 6.98(1H, d, J=8.3Hz), 3.85(3H, s), 3.40–3.28(4H, m); MP: 158–159 | |
| 51 | Ex4 | 3-Cl-4-OMe-Ph | NMR1: 6.98(1H, d, J=8.8Hz), 3.86 (3H, s), 3.13–3.24(4H, m); MP: 158–159 | |
| 52 | Ex4 | 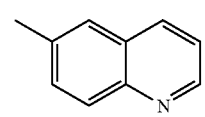 | NMR1: 7.57(1H, dd, J=8.3, 2.4Hz), 6.94(1H, d, J=9.7Hz), 3.86–3.74 (4H, m); MP: 161 | |
| 53 | Ex4 | 4-Ac-3-CF₃-Ph | NMR2: 2.52(3H, s), 3.82(3H, s), 7.83(1H, d, J=8.7Hz); MP: 142–143 | |
| 54 | Ex4 | 3-F-4-OMe-Ph | NMR1: 6.97(1H, d, J=8.3Hz), 3.85 (3H, s), 3.13–3.24(4H, m); MP: 155–156 | |
| 55 | Ex4 |  | NMR1: 8.74(1H, dd, J=4.4, 1.5Hz), 3.97(3H, s), 3.95(3H, s), 3.50–3.38 (4H, m); MP: 144–145 | |

TABLE 7-continued
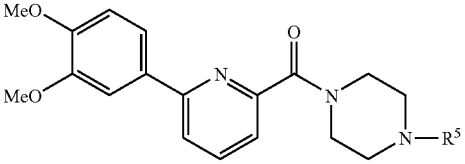
| Ex | Syn | R⁵ | Dat | Sal |
|---|---|---|---|---|
| 56 | Ex4 | 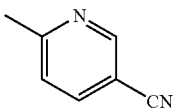 | NMR2: 3.85(3H, s), 4.03–4.21(4H, m), 6.46–6.49(2H, m); MP: 187–188 | |
| 57 | Ex4 | 4-SO₂NH₂-Ph | NMR2: 3.85(3H, s), 7.05–7.10(5H, m), 7.65(2H, d, J=9.3Hz); MP: 213–214 | |
| 58 | Ex3 | 4-Ac-3-OH-Ph | NMR2: 2.49(3H, s), 3.86(3H, s), 12.76(1H, s); MP: 135–137 | |
| 59 | Ex4 | 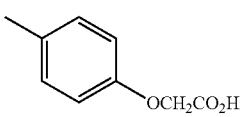 | NMR1: 8.43(1H, d, J=1.9Hz), 3.90 (3H, s), 3.87–3.82(4H, m); MP: 162–163 | |
| 60 | Ex6 | 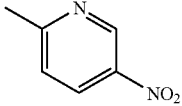 | NMR2: 3.84(3H, s), 4.58(2H, s), 12.90(1H, br s); MP: 143–145 | H₂O |
| 61 | Ex4 | 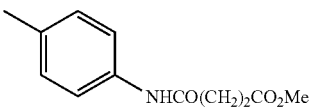 | NMR1: 9.04(1H, d, J=2.9Hz), 6.98 (1H, d, J=8.3Hz), 6.61(1H, d, J=9.2 Hz); MP: 183–184 | |
| 62 | Ex3 | 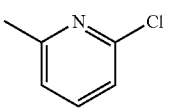 | NMR2: 2.56–2.59(4H, m), 3.59(3H, s), 9.78(1H, s); MP: 140–142 | |
| 63 | Ex4 | 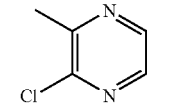 | NMR1: 6.52(1H, d, J=8.3Hz), 3.99 (3H, s), 3.95(3H, s), 3.75–3.68(4H, m); MP: 107–109 | |
| 64 | Ex4 | 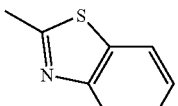 | NMR1: 8.15(1H, d, J=2.4Hz), 6.97 (1H, d, J=8.3Hz), 3.55–3.64(4H, m); MP: 140–142 | |
| 65 | Ex4 | 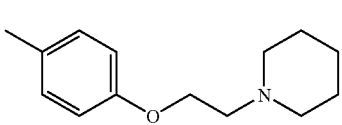 | NMR1: 7.09–7.13(1H, m), 6.98(1H, d, J=8.3Hz), 3.79–3.83(4H, m); MP: 172–173 | |
| 66 | Ex10 |  | NMR2: 1.71–1.76(4H, m), 3.82(3H, s), 4.26(2H, t, J=4.9Hz); MP: 161–165 | 1.5 Ox |
| 67 | Ex14 | 2-Cl-4-Ac-Ph | NMR1: 7.04(1H, d, J=8.3Hz), 6.97 (1H, d, J=8.3Hz), 2.56(3H, s); MP: 164–165 | |

TABLE 7-continued
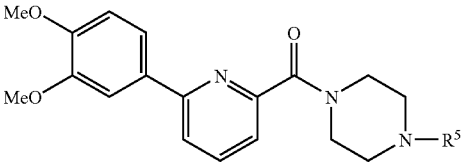
| Ex | Syn | R⁵ | Dat | Sal |
|---|---|---|---|---|
| 68 | Ex4 | 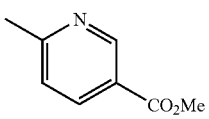 | NMR1: 8.81(1H, d, J=2.5Hz), 3.98 (3H, s), 3.95(3H, s), 3.88(3H, s); MP: 157–159 | |
| 69 | Ex4 | 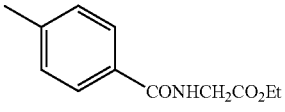 | NMR2: 1.20(3H, t, J=6.9Hz), 3.82 (3H, s), 8.63–8.66(1H, m); MP: 83–85 | |
| 70 | Ex6 | 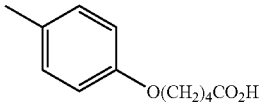 | NMR2: 1.59–1.73(4H, m), 3.85(3H, s), 12.02(1H, s); MP: 79–81 | H₂O |
| 71 | Ex14 | 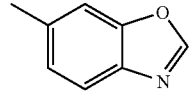 | NMR1: 7.98(1H, s), 6.98(1H, d, J=8.3Hz), 3.28–3.41(4H, m); MP: 151–153 | |
| 72 | Ex12 | 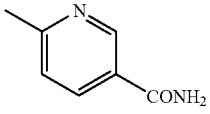 | NMR2: 7.78(1H, br), 7.16(1H, br), 6.88(1H, d, J=8.8Hz), 3.87(3H, s); MP: 243–244 | |
| 73 | Ex3 | 4-CH₂OH-Ph | NMR2: 3.82(3H, s), 4.39(2H, d, J=5.9Hz), 4.96(1H, t, J=5.9Hz); MP: 150–152 | |
| 74 | Ex4 | 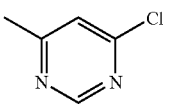 | NMR1: 8.41(1H, s), 6.98(1H, d, J=8.3Hz), 3.98(3H, s); MP: 119–120 | |
| 75 | Ex10 | 4-Ac-3-OMe-Ph | NMR2: 2.44(3H, s), 3.88(3H, s), 6.53(1H, s); MP: 117–118 | 0.5 H₂O |
| 76 | Ex4 | 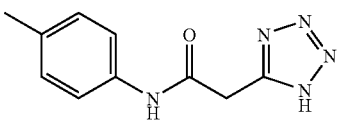 | NMR2: 4.09(2H, S), 10.23(1H, s), 16.22(1H, br); MP: 217–219 | 0.5 H₂O |
| 77 | Ex4 | 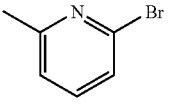 | NMR1: 6.55(1H, d, J=8.3Hz), 4.00 (3H, s), 3.95(3H, s), 3.75–3.66(4H, m); MP: 144–145 | |
| 78 | Ex4 | 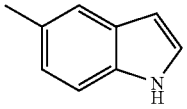 | NMR1: 7.32(1H, d, J=8.8Hz), 3.96 (3H, s), 3.94(3H, s), 3.31–3.18(4H, m); MP: 193–194 | |
| 79 | Ex6 | 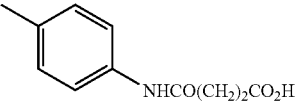 | NMR2: 3.85(3H, s), 9.75(1H, s), 12.09(1H, br); MP: 167–170 | |

TABLE 7-continued

[Structure: 3,4-dimethoxyphenyl-pyridine-2-carbonyl-piperazine-N-R⁵]

| Ex | Syn | R⁵ | Dat | Sal |
|---|---|---|---|---|
| 80 | Ex6 | 4-Me-Ph-O(CH₂)₆CO₂H | NMR2: 1.28–1.43(4H, m), 3.85(3H, s), 11.97(1H, br s); MP: 102–109 | H₂O |
| 81 | Ex4 | 4-Me-pyrimidin-2-yl-O(CH₂)₂NMe₂ | NMR2: 4.53(1H, t, J=4.9Hz), 3.88 (3H, s), 3.83(3H, s), 3.31–3.18(4H, m), 2.81(6H, s); MP: 180–181 | Ox |
| 82 | Ex4 | 2-OMe-Ph | NMR2: 3.79(3H, s), 3.85(3H, s), 6.87–7.02(4H, m); MP: 162–163 | |
| 83 | Ex6 | 3-Me-Ph-O(CH₂)₃CO₂H | NMR2: 1.91(2H, quintet, J=6.8Hz), 3.85(3H, s), 12.12(1H, br s); MP: 109–112 | |
| 84 | Ex6 | 4-Me-2-oxo-pyrimidin-1-yl-(CH₂)₃CO₂H | NMR2: 6.13(1H, d, J=7.3Hz), 3.87 J=7.6Hz); MP: 182–185 | |
| 85 | Ex6 | 6-Me-pyridin-3-yl-O(CH₂)₃CO₂H | NMR1: 7.93(1H, d, J=2.9Hz), 3.97 (3H, s), 3.94(3H, s), 2.57(1H, t, J=7.1Hz); MP: 122–124 | |
| 86 | Ex10 | 4-Me-Ph-O(CH₂)₂NEt₂ | NMR2: 1.22(6H, t, J=7.3Hz), 3.45–3.48(2H, m), 3.82(3H, s); MP: 97–99 | 2 Ox H₂O |
| 87 | Ex6 | 6-Me-pyridin-3-yl-(CH₂)₂CO₂H | NMR1: 6.97(1H, d, J=8.8Hz), 6.63 (1H, d, J=8.8Hz), 2.61(2H, t, J=7.3Hz); MP: 190–191 | |
| 88 | Ex6 | 2-Me-Ph-O(CH₂)₄CO₂H | NMR2: 1.66–1.80(4H, m), 3.82(3H, s), 12.01(1H, s); MP: 176–178 | |
| 89 | Ex12 | 4-(CONHMe)-Ph | NMR2: 2.75(3H, d, J=3.5Hz), 3.85(3H, s), 8.13–8.18(1H, m); MP: 140–141 | |
| 90 | Ex6 | 6-Me-2-Br-pyridin-3-yl-O(CH₂)₃CO₂H | NMR1: 7.14(1H, d, J=8.8Hz), 4.00 (3H, s), 3.95(3H, s), 2.65(1H, t, J=7.1Hz); MP: 189–191 | |

TABLE 7-continued
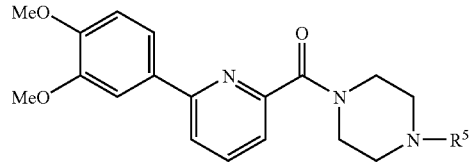
| Ex | Syn | R⁵ | Dat | Sal |
|---|---|---|---|---|
| 91 | Ex15 | 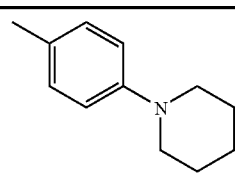 | NMR2: 1.45–1.52(2H, m), 3.85(3H, s), 6.83–6.88(4H, m); MP: 135–137 | 0.5 H₂O |
| 92 | Ex4 | 4-NEt₂-Ph | NMR2: 1.30(6H, t, J=7.0Hz), 3.23 (4H, q, J=7.0Hz), 3.82(3H, s); MP: 84–87 | |
| 93 | Ex12 | 4-(CONMe₂)-Ph | NMR2: 2.95(6H, s), 3.82(3H, s), 7.32(2H, d, J=8.3Hz); MP: 81–83 | H₂O |
| 94 | Ex10 | 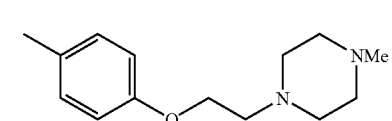 | NMR2: 2.71(3H, s), 3.82(3H, s), 4.04(2H, t, J=5.3Hz); MP: 183(dec) | 2 Ox H₂O |
| 95 | Ex10 | 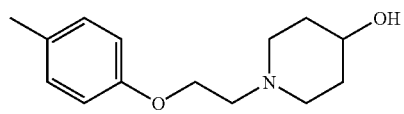 | NMR2: 1.33–1.42(2H, m), 3.82(3H, s), 4.52(1H, d, J=3.9Hz); MP: 143–144 | |
| 96 | Ex4 | 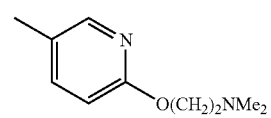 | NMR2: 6.80(1H, d, J=8.8Hz), 3.85 (3H, s), 3.82(3H, s), 2.78(6H, s); MP: 114–115 | Ox H₂O |
| 97 | Ex21 | 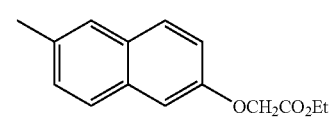 | NMR2: 6.97(1H, d, J=8.6Hz), 4.71 (2H, s), 1.31(3H, t, J=7.3Hz); MP: 140–142 | |
| 98 | Ex6 | 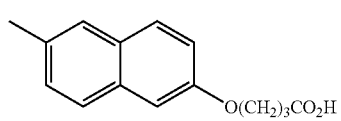 | NMR1: 6.97(1H, d, J=8.3Hz), 3.96 (3H, s), 3.94(3H, s), 2.63(2H, t, J=7.4Hz); MP: 153–154 | |
| 99 | Ex21 | 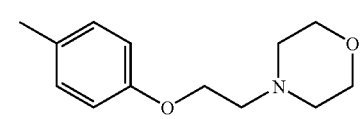 | NMR2: 7.35(1H, dd, J=9.0, 3.4Hz), 4.19(2H, t, J=5.4Hz), 2.78–2.76(4H, m); MP: 163–165 | Ox 0.5 H₂O |
| 100 | Ex10 | 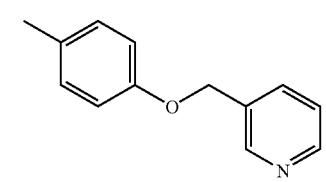 | NMR2: 3.82(3H, s), 5.09(2H, s), 6.94(4H, s); MP: 137–139 | |
| 101 | Ex10 | 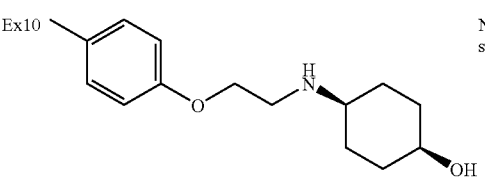 | NMR2: 1.12–1.23(2H, m), 3.82(3H, s), 6.90–6.97(4H, m) MP: 202–205 | Ox 0.5 H₂O |

TABLE 7-continued

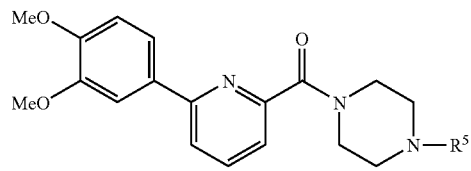

| Ex | Syn | R⁵ | Dat | Sal |
|---|---|---|---|---|
| 102 | Ex10 | [4-methylphenyl-O-CH₂CH₂-N(pyrrolidine-3-OH)] | NMR2: 2.15(1H, br), 3.82(3H, s), 4.23(2H, t, J=5.3Hz),; F: 533 | 2 Ox |
| 103 | Ex10 | [4-methylphenyl-O(CH₂)₂OMe] | NMR2: 3.30(3H, s), 3.82(3H, s), 4.00–4.02(2H, m),; MP: 104–108 | |
| 104 | Ex10 | [4-methylphenyl-O-CH₂-(4-pyridyl)] | NMR2: 3.82(3H, s), 5.12(2H, s), 6.93(4H, s); MP: 140–142 | |
| 105 | Ex21 | [6-methylnaphthyl-O-CH₂CH₂-morpholine] | NMR2: 7.37(1H, dd, J=8.8, 2.4Hz), 4.28(2H, t, J=5.4Hz), 3.85(3H, s), 3.82(3H, s); MP: 167–173 | Ox 0.5 H₂O |
| 106 | Ex6 | [6-methyl-2-methylquinoline] | NMR2: 8.76(1H, d, J=8.8Hz), 3.86(3H, s), 3.83(3H, s), 2.91(3H, s); MP: 135–140 | HCl H₂O |
| 107 | Ex10 | [4-methylphenyl-O-CH₂-(pyridine N-oxide)] | NMR2: 5.06(2H, s), 6.94(4H, s), 8.28(1H, br s); MP: 147–148 | |
| 108 | Ex10 | [4-methylphenyl-O-CH₂CH₂-morpholine] | NMR2: 3.82(3H, s), 4.13–4.16(2H, m), 6.88–6.95(4H, m); MP: 109–111 | 1.5 Ox |
| 109 | Ex10 | [4-methylphenyl-O-CH₂CH₂-N(CH₂CH₂OMe)₂] | NMR2: 3.28(6H, s), 3.82(3H, s), 4.16(2H, t, J=5.4Hz); F: 579 | 2 Ox |
| 110 | Ex10 | [4-methylphenyl-O-CH₂CH₂-thiomorpholine-S,S-dioxide] | NMR2: 3.82(3H, s), 4.00–4.05(2H, m), 6.86(2H, d, J=8.8Hz); MP: 106–109 | 2 Ox 2 H₂O |
| 111 | Ex6 | [4-methylphenyl-NMe(CH₂)₃CO₂H] | NMR2: 2.79(3H, br s), 3.85(3H, s), 12.06(1H, s); MP: 138–139 | H₂O |

TABLE 8
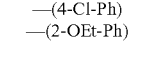
| Ex | Syn | R¹ | R² | Dat | Sal |
|---|---|---|---|---|---|
| 112 | Ex4 | MeO | cPr—CH₂O | NMR1: 7.76(1H, dd, J=8.3, 1.0Hz), 2.53 (3H, s), 0.32–0.38(2H, m); MP: 142–144 | |
| 113 | Ex4 | MeO | Cl | NMR1: 8.08(1H, d, J=2.5Hz), 7.03(1H, d, J=8.8Hz), 2.53(3H, s); MP: 168–170 | |
| 114 | Ex4 | MeO | CHF₂O | NMR1: 7.07(1H, d, J=8.8Hz), 6.62(1H, t, J=74.8Hz), 2.54(3H, s); MP: 160–162 | |
| 115 | Ex4 | MeO | F | F: 529 MP: 168–170 | |
TABLE 9
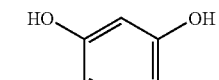
| Ex | R⁵ |
|---|---|
| 116 | —Et |
| 117 | —CHO |
| 118 | —(2-Me-Ph) |
| 119 | —(3-CF₃-Ph) |
| 120 | —(2-F-Ph) |
| 121 | —(4-Cl-Ph) |
| 122 | —(2-OEt-Ph) |
| 123 | 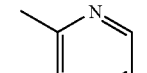 |
| 124 | 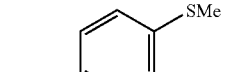 |
| 125 | 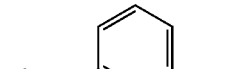 |
| 126 | 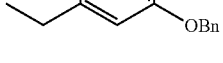 |
| 127 | 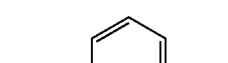 |
| 128 | 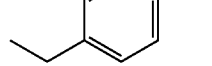 |
TABLE 9-continued
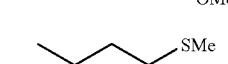
| Ex | R⁵ |
|---|---|
| 129 | 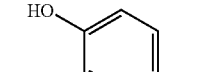 |
| 130 | 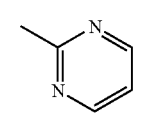 |
| 131 | |
| 132 | |
| 133 | |
| 134 | |

TABLE 9-continued
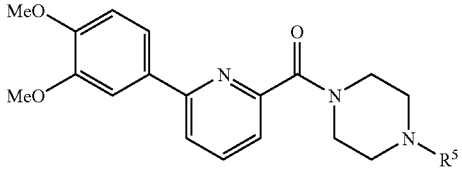
| Ex | R⁵ |
|---|---|
| 135 | 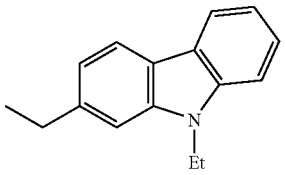 |
| 136 | 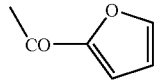 |
| 137 | 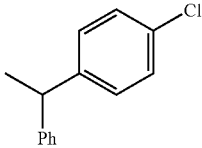 |
| 138 | 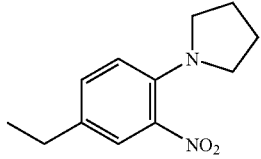 |
| 139 | 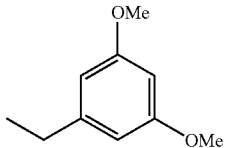 |
| 140 | 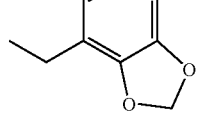 |
| 141 | 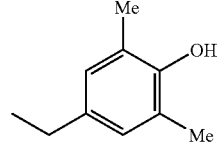 |
| 142 | 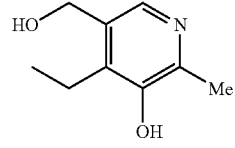 |
TABLE 9-continued
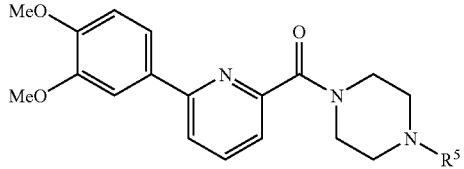
| Ex | R⁵ |
|---|---|
| 143 | 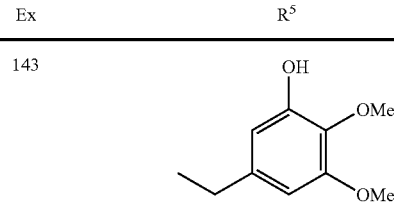 |
| 144 | 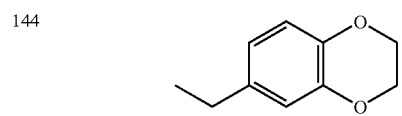 |
| 145 | 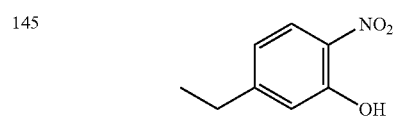 |
| 146 | 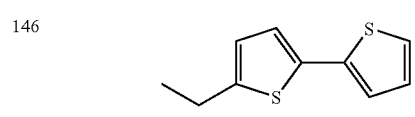 |
| 147 | 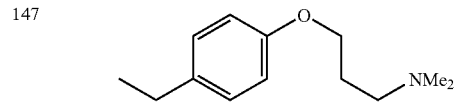 |
TABLE 10
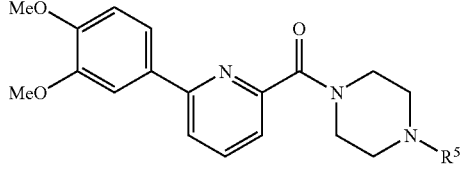
| No | R⁵ |
|---|---|
| 1 | 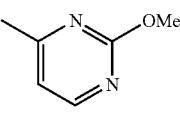 |
| 2 | 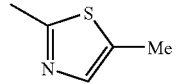 |

TABLE 10-continued

[Structure: 6-(3,4-dimethoxyphenyl)pyridine-2-carbonyl piperazine with N-R⁵]

| No | R⁵ |
|---|---|
| 3 | 3-fluoro-5-methylpyridin-yl |
| 4 | 6-methylquinoxalinyl |
| 5 | 6-methylisoquinolinyl |
| 6 | 7-methylquinazolinyl |
| 7 | 6-methyl-1,2,3,4-tetrahydroquinolinyl |
| 8 | 5-methyl-2,3-dihydro-1H-inden-1-one |
| 9 | 5-methylbenzothiazolyl |
| 10 | 6-methyl-1,2,3,4-tetrahydroisoquinolinyl |

TABLE 10-continued

[Structure: 6-(3,4-dimethoxyphenyl)pyridine-2-carbonyl piperazine with N-R⁵]

| No | R⁵ |
|---|---|
| 11 | 5-methylbenzoxazolyl |
| 12 | 5-methyl-2,3-dihydrobenzofuranyl |

TABLE 11

[Structure: 6-(3,4-dimethoxyphenyl)pyridine-2-carbonyl piperazine with N-phenyl bearing R' at positions 2–6]

| No | R' |
|---|---|
| 13 | 4-Pip |
| 14 | 4-O(CH₂)₃-Pipr |
| 15 | 4-(CH₂)₃CO₂H |
| 16 | 4-Pyrr |
| 17 | 4-SO(CH₂)₂-Mor |
| 18 | 4-CH₂NMe₂ |
| 19 | 4-O(CH₂)₃-Pip |
| 20 | 4-SO(CH₂)₂-Pipr |
| 21 | 4-NMeCH₂CO₂H |
| 22 | 4-O(CH₂)₃-Pyrr |
| 23 | 4-SO₂(CH₂)₂-Mor |
| 24 | 4-O(CH₂)₃(4-Me-Pipr) |
| 25 | 4-SO(CH₂)₂-Pip |
| 26 | 4-SO₂(CH₂)₂-Pipr |
| 27 | 4-SO(CH₂)₂NMe₂ |
| 28 | 4-SO(CH₂)₂-Pyrr |
| 29 | 4-NH(CH₂)₂-Mor |
| 30 | 4-SO(CH₂)₂(4-Me-Pipr) |
| 31 | 4-SO₂(CH₂)₂-Pip |
| 32 | 4-NH(CH₂)₂-Pipr |
| 33 | 4-SO₂(CH₂)₂NMe₂ |
| 34 | 4-SO₂(CH₂)₂-Pyrr |
| 35 | 4-NMe(CH₂)₂-Mor |
| 36 | 4-SO₂(CH₂)₂(4-Me-Pipr) |
| 37 | 4-NH(CH₂)₂-Pip |
| 38 | 4-NMe(CH₂)₂-Pipr |
| 39 | 4-NH(CH₂)₂NMe₂ |
| 40 | 4-NH(CH₂)₂-Pyrr |
| 41 | 4-CO-Mor |
| 42 | 4-NH(CH₂)₂(4-Me-Pipr) |
| 43 | 4-NMe(CH₂)₂-Pip |
| 44 | 4-CO-Pipr |
| 45 | 4-NMe(CH₂)₂NMe₂ |
| 46 | 4-NMe(CH₂)₂-Pyrr |
| 47 | 3-CH=CHCO₂H |

TABLE 11-continued

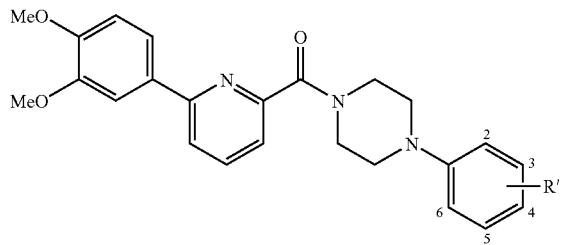

| No | R' |
|---|---|
| 48 | 4-NMe(CH$_2$)$_2$(4-Me-Pipr) |
| 49 | 4-NHCH$_2$CO$_2$H |
| 50 | 2-F-4-OMe |
| 51 | 4-CO(4-Me-Pipr) |
| 52 | 4-(4-Me-Pipr) |
| 53 | 2-Me-4-OMe |
| 54 | 4-CONH(CH$_2$)$_2$NMe$_2$ |
| 55 | 3-CO$_2$H |
| 56 | 3-Ac-4-OMe |
| 57 | 3-NMe$_2$ |
| 58 | 3-Me-4-OMe |
| 59 | 3,4-diCl |
| 60 | 3-NHCO(CH$_2$)$_2$NEt$_2$ |
| 61 | 3-Ac-4-OH |
| 62 | 2,4-diF |
| 63 | 3-NHCO-Pip4 |
| 64 | 2,4-diCl |
| 65 | 2,3-diOMe |
| 66 | 3,4-(OCH$_2$O) |
| 67 | 2,3-diF |
| 68 | 2,3-diCl |
| 69 | 3,4-diF |
| 70 | 3,5-diF |
| 71 | 3,5-diCl |
| 72 | 2,4-diOMe |
| 73 | 3,4-diOMe |
| 74 | 3,5-diOMe |
| 75 | 3,4,5-triOMe |

TABLE 12

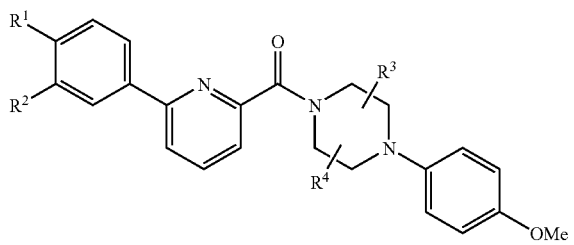

No: 76
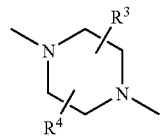

No: 77
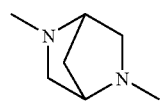

No: 78
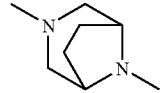

TABLE 12-continued

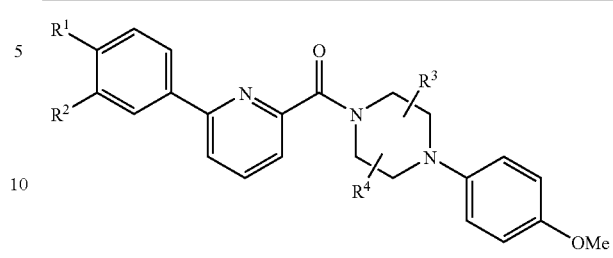

No: 79
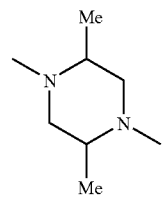

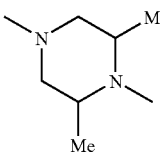

TABLE 13

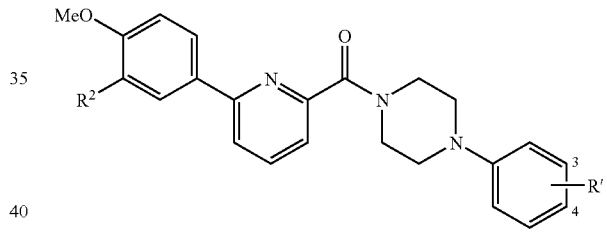

| No | R' |
|---|---|
| | R$^2$ = cPr—CH$_2$—O— |
| 80 | 4-OCF$_3$ |
| 81 | 4-OCHF$_2$ |
| 82 | 4-Ac |
| 83 | 4-CH$_2$CO$_2$H |
| 84 | 4-Mor |
| 85 | 4-(CH$_2$)$_3$CO$_2$H |
| 86 | 4-OCH$_2$CO$_2$H |
| 87 | 4-Pipr |
| 88 | 4-O(CH$_2$)$_3$CO$_2$2H |
| 89 | 4-Pip |
| 90 | 4-NHCH$_2$CO$_2$H |
| 91 | 4-CH$_2$NMe$_2$ |
| 92 | 4-Pyrr |
| 93 | 4-(4-Me-Pipr) |
| 94 | 4-NMeCH$_2$CO$_2$H |
| 95 | 4-CO$_2$H |
| 96 | 3-Cl |
| 97 | 4-CO(4-Me-Pipr) |
| 98 | 3-OMe |
| 99 | 3-F |
| 100 | 4-CONH(CH$_2$)$_2$NMe$_2$ |
| | R$^2$ = Cl |
| 101 | 4-OMe |
| 102 | 4-Cl |
| 103 | 4-F |
| 104 | 3-OCF$_3$ |

TABLE 13-continued

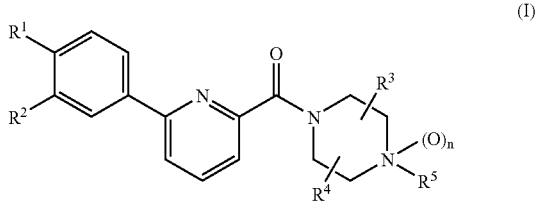

| No  | R'              |
|-----|-----------------|
| 105 | 3-Ac            |
| 106 | 3-O(CH$_2$)$_2$NMe$_2$ |

What is claimed is:

1. A pyridine derivative represented by the following general formula (I) or a pharmaceutically acceptable salt thereof:

(I)

wherein each symbol has the following meaning:
R$^1$: O-a lower alkyl,
R$^2$: O-a lower alkyl or O-a lower alkylene-a hydrocarbon ring,
R$^3$ and R$^4$: the same or different from each other, H, or a lower alkyl,
R$^5$: an optionally substituted phenyl or an optionally substituted heterocycle selected from the group consisting of pyridine, thiazole, pyrazine, pyrimidine, benzofuran, piperidine, pyridazine, quinoline, 2,3-dihydro-1,4-benzodioxine, benzothiazole, benzoxazole and indole,
wherein the substituent in the optionally substituted phenyl and the optionally substituted heterocycle is a group selected from the following G group:
G group: groups represented by (i) —X-a C$_{1-6}$ alkylene-A, (ii) -a C$_{1-6}$ alkylene-A, or (iii) —B,
wherein X is O, S, SO, SO$_2$, NH, N(a C$_{1-6}$ alklyl), SO$_2$NH, SO$_2$N(a C$_{1-6}$ alkyl), NHSO$_2$, N(a C$_{1-6}$ alkyl) SO$_2$, CO, CO$_2$, O—CO, CONH, CON(a C$_{1-6}$ alkyl), NHCO, N(a C$_{1-6}$ alkyl )CO or NHCONH,
A is —CN, —OH, —CO$_2$H, —CO$_2$-a C$_{1-6}$ alkyl, —NO$_2$, —SO$_3$H, —NH$_2$, —CONH$_2$, —SO$_2$NH$_2$, a C$_{1-6}$ alkyl substituted with halogen(s), —NH-a C$_{1-6}$ alkylene-O-a C$_{1-6}$ alkyl, —N(a C$_{1-6}$ alkyl)-a C$_{1-6}$ alkylene-O-a C$_{1-6}$ alkyl, —N(—C$_{1-6}$ alkylene-O-a C$_{1-6}$ alkyl)$_2$, -a hydrocarbon ring, -a heterocycle selected from the group consisting of morpholine, pyridine, pyridine-N-oxide, piperidine, piperazine, tetrazole, pyrrolidine and thiomorpholine, —X-a C$_{1-6}$ alkyl, —X-a C$_{1-6}$ alkyl substituted with halogen(s), —X-a hydrocarbon ring, —X-a heterocycle selected from the group consisting of morpholine, pyridine, pyridine-N-oxide, piperidine, piperazine, tetrazole, pyrrolidine and thiomorpholine, —X-a C$_{1-6}$ alkylene-CN, —X-a C$_{1-6}$ alkylene-OH, —X-a C$_{1-6}$ alkylene-CO$_2$H, —X-a C$_{1-6}$ alkylene-CO$_2$-a C$_{1-6}$ alkyl, —X-a C$_{1-6}$ alkylene-NO$_2$, —X-a C$_{1-6}$ alkylene-SO$_3$, —X-a C$_{1-6}$ alkylene-NH$_2$, —X-a C$_{1-6}$ alkylene-CONH$_2$, —X-a C$_{1-6}$ alkylene-SO$_2$NH$_2$, —X-a C$_{1-6}$ alkylene-a hydrocarbon ring or —X-a C$_{1-6}$ alkylene-a heterocycle selected from the group consisting of morpholine, pyridine, pyridine-N-oxide, piperidine, piperazine, tetrazole, pyrrolidine and thiomorpholine, B is -a C$_{1-6}$ alkyl, -a halogen, a C$_{1-6}$ alkyl substituted with halogen(s), or a group described in A, and
the hydrocarbon ring and heterocycle in the above A and B may have from 1 to 5 substituents selected from the group consisting of a C$_{1-6}$ alkyl, a halogen, a C$_{1-6}$ alkyl substituted with halogen(s), CN, OH, O-a C$_{1-6}$ alkyl, NH$_2$, —NH-a C$_{1-6}$ alkyl, —N(a C$_{1-6}$ alkyl)$_2$, S-a C$_{1-6}$ alkyl, SO-a C$_{1-6}$ alkyl, SO$_2$-a C$_{1-6}$ alkyl, SO$_2$NH$_2$, SO$_2$NH-a C$_{1-6}$ alkyl, SO$_2$N(a C$_{1-6}$ alkyl)$_2$, NHSO$_2$-a C$_{1-6}$ alkyl, CO$_2$H, CO$_2$-a C$_{1-6}$ alkyl, CONH$_2$, CONH-a C$_{1-6}$ alkyl, CON(a C$_{1-6}$ alkyl)$_2$ and NHCO-a C$_{1-6}$ alkyl, and
n: 0.

2. The pyridine derivative or a pharmaceutically acceptable salt thereof according to claim 1, which is selected from the group consisting of 1-[6-(3,4-dimethoxyphenyl )pyridine-2-carbonyl]-4-(4-methoxyphenyl)piperazine, 1-(4-{4-[6-(3-cyclopropylmethoxy-4-methoxyphenyl )pyridine-2-carbonyl]piperazin-1-yl} phenyl )ethanone, 1-(6-bromo-2-pyridyl )-4-[6-(3,4-dimethoxyphenyl)pyridine-2-carbonyl] piperazine, 4'-{4-[6-(3,4-dimethoxyphenyl)pyridine-2-carbonyl]piperazin-1-yl}acetanilide, 3-diethylamino-4'-{4-[6-(3,4-dimethoxyphenyl)pyridine-2-carbonyl]piperazin-1-yl}propananilide, 4-(4-{4-[6-(3,4-dimethoxyphenyl) pyridine-2-carbonyl]piperazin-1-yl}phenyl)morpholine, 1-[2-(4-{4-[6-(3,4-dimethoxyphenyl)pyridine-2-carbonyl] piperazin-1-yl}phenoxy)ethyl]piperidin-4-ol, 4-{2-[(6-(4-[6-(3,4-dimethoxyphenyl)pyridine-2-carbonyl]piperazin-1-yl}-3-pyridyl)oxy ]ethyl}morpholine, trans-5-(4-{4-[6-(3,4-dimethoxyphenyl)pyridine-2-carbonyl]-2,5-dimethylpiperazin-1-yl}phenyl)pentanoic acid and 1-[6-(3, 4-dimethoxyphenyl)pyridine-2-carbonyl]-4-(4-[(1-oxido-4-pyridyl)methoxy]phenyl}piperazine.

3. A pharmaceutical composition which comprises the pyridine derivative according to claim 1 or a pharmaceutically acceptable salt thereof and a pharmaceutically acceptable carrier.

4. A method for treating respiratory disease selected from the group consisting of bronchial asthma and chronic obstructive pulmonary disease (COPD) comprising administering to a subject an effective amount of the pharmaceutical composition according to claim 3.

5. The method according to claim 4, wherein said respiratory disease is bronchial asthma.

6. The method according to claim 4, wherein said respiratory disease is chronic obstructive pulmonary disease (COPD).

7. A pyridinecarboxylic acid derivative represented by the general formula (IIa):

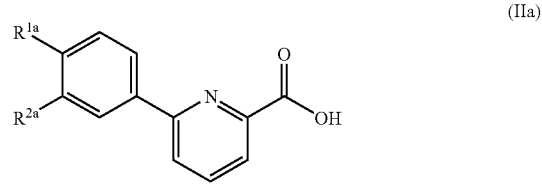

(IIa)

wherein
R$^{1a}$ is O-a lower alkyl, and R$^{2a}$ is O-a lower alkyl or O-a lower alkylene-a hydrocarbon ring.

* * * * *